United States Patent
Bode et al.

(10) Patent No.: US 9,944,750 B2
(45) Date of Patent: Apr. 17, 2018

(54) POLYETHYLENE GLYCOL SUBSTITUTED ACYL BORATES

(71) Applicant: ETH Zurich, Zurich (CH)

(72) Inventors: Jeffrey Bode, Zurich (CH); Hidetoshi Noda, Zurich (CH); Gabor Eros, Zurich (CH); Dmitry Mazunin, Zurich (CH)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 15/110,910

(22) PCT Filed: Jan. 9, 2015

(86) PCT No.: PCT/EP2015/050333
§ 371 (c)(1),
(2) Date: Jul. 11, 2016

(87) PCT Pub. No.: WO2015/104374
PCT Pub. Date: Jul. 16, 2015

(65) Prior Publication Data
US 2017/0022321 A1    Jan. 26, 2017

(30) Foreign Application Priority Data

Jan. 10, 2014  (EP) ..................... 14150784

(51) Int. Cl.
  *C08G 65/337* (2006.01)
  *A61K 38/08* (2006.01)
  *A61K 38/26* (2006.01)
  *A61K 47/48* (2006.01)

(52) U.S. Cl.
  CPC ............ *C08G 65/337* (2013.01); *A61K 38/08* (2013.01); *A61K 38/26* (2013.01); *A61K 47/48215* (2013.01); *C08G 2650/04* (2013.01); *C08L 2203/02* (2013.01)

(58) Field of Classification Search
  CPC ...... C08G 65/337; A61K 38/08; A61K 38/26; A61K 47/48215
  See application file for complete search history.

(56) References Cited

FOREIGN PATENT DOCUMENTS

WO    2012/159106 A2    11/2012

OTHER PUBLICATIONS

Dumas et al.; "Amide-Forming Ligation of Acyltrifluoroborates and Hydroxylamines in Water;" Angew. Chem. Int. Ed.; vol. 51; 2012; pp. 5683-5686; XP002725290 with author manuscript.
Dumas et al.; "Synthesis of Acyltrifluoroborates;" Org. LETT.; vol. 14; 2012; pp. 2138-2141; XP002725291.
Morpurgo et al.; "Selective Alkylation and Acylation of alpha and epsilon Amino Groups with PEG in a Somatostatin Analogue: Tailored Chemistry for Optimized Bioconjugates;" Bioconjugate Chem.; ACS; Washington, DC, US; vol. 13; Oct. 29, 2002; pp. 1238-1243; XP008040597.
Roy et al.; "A Comparative Study of Polyol Complexes of Arsenite, Borate, and Tellurate Ions;" J. Inorg. Nucl. Chem.; vol. 4; 1957; pp. 106-114; XP002725292.
Mar. 26, 2015 International Search Report issued in International Patent Application No. PCT/EP2015/050333.
Mar. 26, 2015 Written Opinion issued in International Patent Application No. PCT/EP2015/050333.

*Primary Examiner* — Kahsay Habte
(74) *Attorney, Agent, or Firm* — Oliff PLC

(57) ABSTRACT

Polyethylene glycol substituted acyl borates, methods for their preparation, and the use of the polyethylene glycol substituted acyl borates for the preparation of polyethylene glycol substituted macromolecules. The polyethylene glycol substituted acyl borate has the general formula (I)

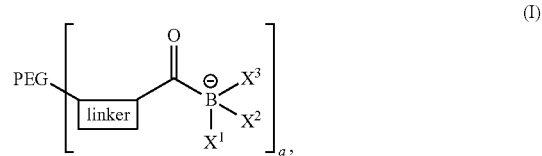

wherein PEG denotes a polyethylene glycol-based substituent; a is an integer from 1 to 12; X1, X2, and X3 are independently of one another selected from the group made of F, OR, N+R3, N+R2OR, N+R2SR, and N+R2NR2, and are optionally forming a cyclic or a bicyclic structure; and R is an organic substituent or H.

15 Claims, 8 Drawing Sheets

SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Peptide Hydroxylamine 13
<220> FEATURE:
<221> NAME/KEY: BLOCKED
<222> LOCATION: (1)..(1)

<400> SEQUENCE: 1

Glu Cys Ala Lys Gln Asp Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Peptide Amide 14
<220> FEATURE:
<221> NAME/KEY: AMIDATION
<222> LOCATION: (1)..(1)

<400> SEQUENCE: 2

Glu Cys Ala Lys Gln Asp Phe
1               5

<210> SEQ ID NO 3
<211> LENGTH: 31
<212> TYPE: PRT
<213> ORGANISM: Artificial Sequence
<220> FEATURE:
<223> OTHER INFORMATION: Amino Acids 7-37 of GLP-1

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: AMIDATION
<222> LOCATION: (20)..(20)

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Peptide 15
<220> FEATURE:
<221> NAME/KEY: Orn_BLOCKED
<222> LOCATION: (20)..(20)

```
<400> SEQUENCE: 5

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30
```

POLYETHYLENE GLYCOL SUBSTITUTED ACYL BORATES

TECHNICAL FIELD

The present invention refers to polyethylene glycol substituted acyl borates, to methods for their preparation, and to the use of said polyethylene glycol substituted acyl borates for the preparation of polyethylene glycol substituted macromolecules.

BACKGROUND

PEGylated peptides and other macromolecules —i.e. macromolecules bearing a polyethylene glycol (PEG) substituent—are widely used, in particular for the preparation of pharmaceuticals, drug delivery vehicles, and other biocompatible materials.

For the purposes of pharmaceutical development, the most common conjugation reaction is the addition of thiols (i.e. cysteine side chains) to a drug, or PEG reagent bearing an electrophilic moiety such as a maleimide or alpha-halo amide. Other solutions include oxime formation (the reaction of a hydroxylamine with a ketone or aldehyde) and non-specific amide formation on lysine side chains. Chemoselective conjugations using the triazole forming reactions of azides and terminal alkynes are also popular, at least in academic research. The main limitations are either the need for toxic copper reagents or slow rate constants requiring an excess of one of the reagents.

Since both the macromolecules and the polyethylene glycol substituents tend to be expensive and complex in preparation, it is important that the PEGylation is selective and highly efficient. Furthermore, it is desirable that a stable natural bond is formed, i.e. a bond that is commonly encountered in naturally occurring materials and which is known to be stable and safe for use in medical and materials applications.

Chemical reactions that allow selective bond formation between two reactants even in the presence of many unprotected functional groups are important but rare. The ideal chemoselective conjugation reaction would allow rapid covalent bond formation between two unique but chemically stable moieties under aqueous conditions using equimolar amounts of the ligation partners, regardless of the size of the substrate or number and nature of unprotected functional groups.

Such feats of bond construction, such as DNA ligation, are routinely accomplished by specific biochemical enzymes and can, in certain circumstances, be co-opted for synthetic applications. But fast, selective strictly chemical ligations are so far unknown. The few known synthetic ligations form unnatural bonds, require the presence of toxic reagents, or do not proceed fast enough to conjugate equimolar quantities of large or valuable starting materials.

Therefore, one of the remaining challenges in this area is the identification of faster ligations (second order rate constants >10 $M^{-1}$ $s^{-1}$) that form natural bonds, preferably under aqueous conditions, without added reagents or catalysts.

More general, the technical problem to be solved by the present invention is the selective formation of a covalent bond between two large molecules. This technical problem occurs frequently in the synthesis of biologically active molecules including, but not limited to, proteins, peptides, PEGylated biomolecules and peptides, antibody drug conjugates, and functionalized polymers. Typical reactions for covalent bond formation suffer from three problems that make this difficult:

a. Most organic reactions require anhydrous, organic solvents and do not operate properly in the presence of unprotected organic functional groups (i.e. amines, carboxylic acids, alcohols, thiols, etc.).
b. Most organic reactions for joining large molecules are too slow, requiring high concentrations (10 mM or higher), long reaction times, a large excess of one reactant, and/or high temperatures.
c. The best known solutions for joining two large, unprotected molecules give an unnatural connectivity that can be problematic, immunogenic, or which cannot be used to make the natural forms of molecules such as proteins.

In order to join large molecules using equimolar amounts of each reactant—which is important for economic and purification reasons—a second order rate constant of at least 1 $M^{-1}$ $s^{-1}$ is required. Faster rate constants are even more desirable.

SUMMARY

It is therefore a problem of the present invention to provide a means for the preparation of polyethylene glycol substituted macromolecules, which allows for a simple, fast, selective, and efficient synthesis, preferably forming a natural bond.

This problem is solved by the polyethylene glycol substituted acyl borates of the present invention, which allow for the formation of an amide bond between the polyethylene glycol unit and a macromolecule bearing a hydroxylamine moiety.

BRIEF DESCRIPTION OF DRAWINGS

FIG. 7b is a HPLC analysis of purified PEGylated peptide 16a.
FIG. 7c is a MALDI analysis of purified PEGylated peptide 16a.

DETAILED DESCRIPTION

Figure 1A:
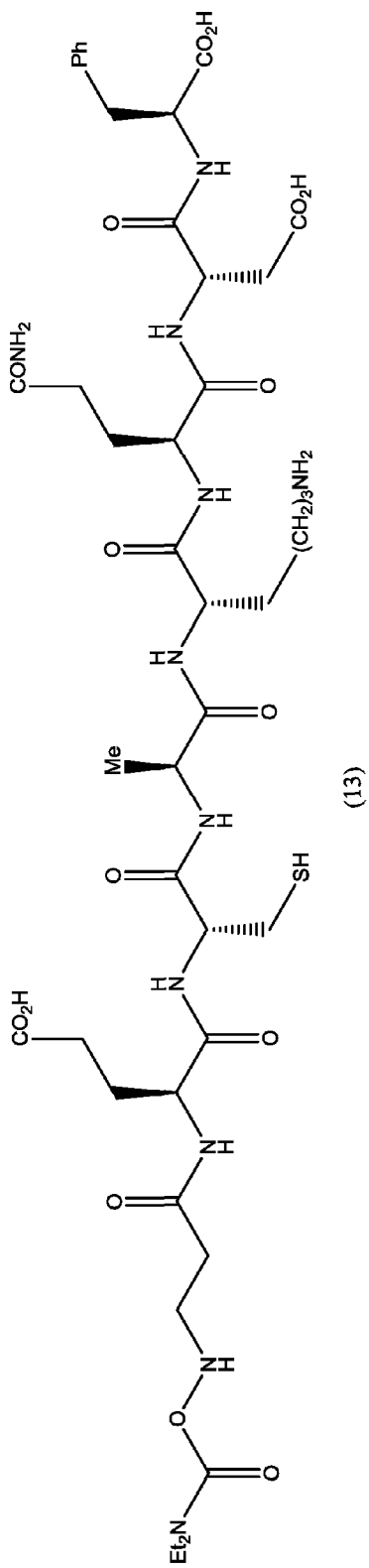
FIG. 1a is a diagram of the chemical structure of a peptide hydroxylamine 13 produced by Example 3.

These polyethylene glycol substituted acyl borates have the general formula (I)

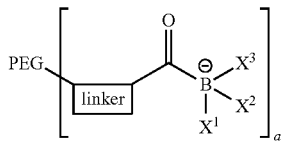

In said formula (I), PEG denotes a polyethylene glycol-based substituent; a is an integer from 1 to 12; $X^1$, $X^2$, and $X^3$ are independently of one another selected from the group consisting of F, OR, $N^+R_3$, $N^+R_2OR$, $N^+R_2SR$, and $N^+R_2NR_2$, and are optionally forming a cyclic or a bicyclic structure; and R is an organic substituent or H.

Typically, a counterion will also be present if there is no dative bond or cation within the ligand on boron, such as preferentially $K^+$ or $Cs^+$, but also $Li^+$, $Na^+$, $R_4N^+$, $R_4P^+$ or $R_3S^+$=O.

Throughout this application, "PEG" refers to a polyethylene glycol-based compound or substituent of any length, having a backbone at least essentially consisting of ethylene glycol units (—(CH$_2$)$_2$O—) and optionally carrying further substituents. Said PEG moiety carries at least one, and up to twelve, acyl borate substituents.

The term "linker" as used in this application denotes an optionally present linker group. Each acyl borate substituents may or may not be attached to such a linker, independently of the other acyl borates, if present. Said linker group is generally an organic or hetero-organic moiety, and is preferably a $C_1$-$C_{20}$ hydrocarbon optionally containing 1 or 2 aromatic rings.

Throughout this application, the term "organic substituent" refers to a hydrocarbon based-moiety, which is covalently attached to the remainder of a compound and which may optionally also comprise one or more heteroatoms.

The polyethylene glycol substituted acyl borates of the present invention have been found to selectively react with hydroxylamines to form an amide bond. In particular, this ligation reaction is not only highly chemoselective, such that it may be used for connecting molecules bearing a variety of unprotected functional groups, but also extremely fast: A second order rate constant of >20 $M^{-1}s^{-1}$ has been measured for this reaction.

Furthermore, the ligation forming the amide bond occurs upon simple mixing the polyethylene glycol substituted acyl borate of the present invention with a hydroxylamine in water or other aqueous media.

Therefore, the present invention provides a new chemical reaction that forms amide bonds, one of the most common organic functional groups in biological systems, without the need for chemical reagents and which operates rapidly in water and even in the presence of unprotected organic functional groups.

Consequently, these reactions enable selective conjugations of large molecules at micromolar concentrations using equimolar amounts of reactants, opening an avenue to the synthesis of much larger, structurally defined molecules including multidomain proteins, protein-polymer conjugates, and oligomeric biomolecules bearing polyethylene glycol substituents.

The main advantages of the present invention are:
1. Formation of stable, natural amide bonds at the ligation site;
2. excellent chemoselectivity allowing the reaction to work in the presence of unprotected amines, carboxylic acids, thiols, alcohols, etc.;
3. rapid ligations in water without the need for any reagents or catalysts;
4. very fast reaction kinetics, making it suitable for conjugating together large molecules at 1:1 stochiometry; and
5. facile introduction of the requisite acyl borate into reagents of interest (i.e. PEGs, dyes, affinity tags, etc.) by a simple, inexpensive process.

The polyethylene glycol substituted acyl borate of the present invention may contain one or several acyl borate moieties, in particular from 1 to 12. Thus, the coefficient "a" in formula (I) may be any integer number from 1 to 12. Preferably, a is from 1 to 8, more preferably from 1 to 4, and most preferred a=1.

According to a first preferred embodiment, all three substituents $X_1$, $X_2$ and $X_3$ are F. Thus, preferably, the acyl borate of the present invention is a trifluoroborate. These compounds have been found to be particularly reactive towards hydroxylamines, thus displaying extremely short reaction times. Also, the acyl trifluoroborates have proven to be surprisingly stable and easy to handle.

More preferably, the compound of the present invention is a polyethylene glycol substituted potassium acyl trifluoroborate.

The ligation of small and relatively simple acyl trifluoroborates with hydroxylamines has been described before (Dumas, A. M., Molander, G. A., Bode, J. W. "Amide-Forming Ligation of Acyltrifluoroborates and Hydroxylamines in Water", *Angew. Chem. Int. Ed.* 2012, 51, 5683-5686). However, this type of reaction has never been used for coupling large or structurally complex molecules.

A method for the preparation of acyl trifluoroborates starting from aldehydes has also been described (Dumas, A. M.; Bode, J. W. "Synthesis of Acyltrifluoroborates", *Org. Lett.* 2012, 14, 2138-2141). The contents of said publication in this respect are herewith incorporated by reference.

According to a second preferred embodiment, $X^1$ is F, and $X^2$ and $X^3$ are OR. Preferably, $X^2$ and $X^3$ are further forming a five- or six-membered heterocycle.

More preferably, the polyethylene glycol substituted acyl borate of the second preferred embodiment is selected from the group consisting of (II) to (XI)

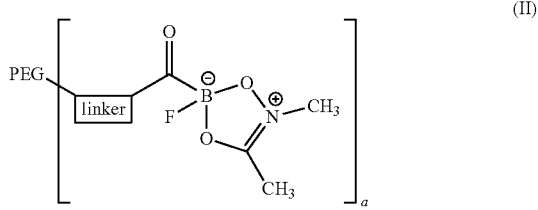

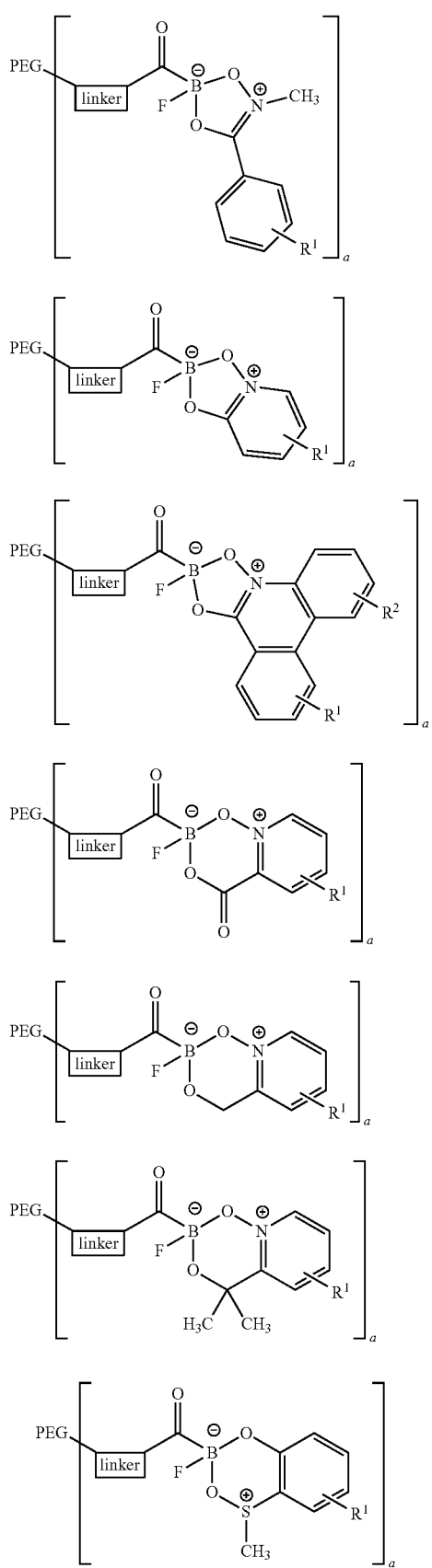

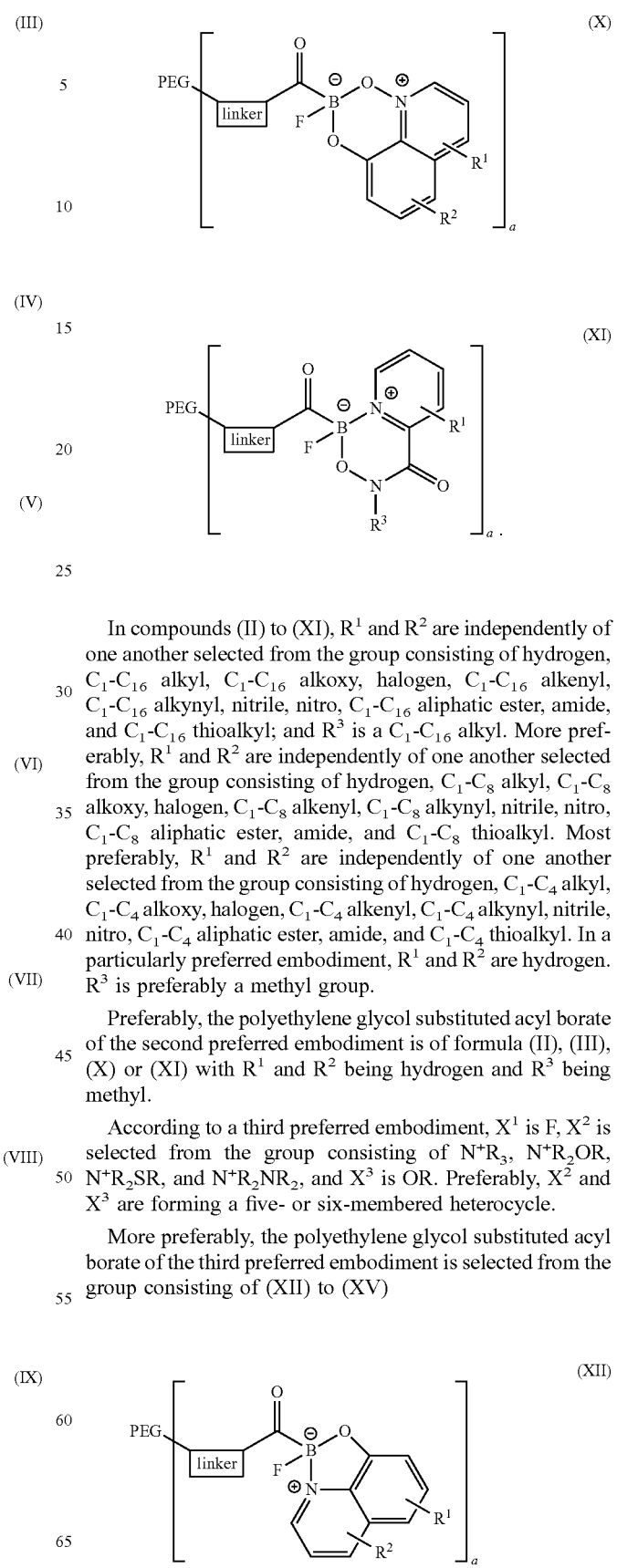

In compounds (II) to (XI), $R^1$ and $R^2$ are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl; and $R^3$ is a $C_1$-$C_{16}$ alkyl. More preferably, $R^1$ and $R^2$ are independently of one another selected from the group consisting of hydrogen, $C_1$-$C_8$ alkyl, $C_1$-$C_8$ alkoxy, halogen, $C_1$-$C_8$ alkenyl, $C_1$-$C_8$ alkynyl, nitrile, nitro, $C_1$-$C_8$ aliphatic ester, amide, and $C_1$-$C_8$ thioalkyl. Most preferably, $R^1$ and $R^2$ are independently of one another selected from the group consisting of hydrogen, $C_1$-$C_4$ alkyl, $C_1$-$C_4$ alkoxy, halogen, $C_1$-$C_4$ alkenyl, $C_1$-$C_4$ alkynyl, nitrile, nitro, $C_1$-$C_4$ aliphatic ester, amide, and $C_1$-$C_4$ thioalkyl. In a particularly preferred embodiment, $R^1$ and $R^2$ are hydrogen. $R^3$ is preferably a methyl group.

Preferably, the polyethylene glycol substituted acyl borate of the second preferred embodiment is of formula (II), (III), (X) or (XI) with $R^1$ and $R^2$ being hydrogen and $R^3$ being methyl.

According to a third preferred embodiment, $X^1$ is F, $X^2$ is selected from the group consisting of $N^+R_3$, $N^+R_2OR$, $N^+R_2SR$, and $N^+R_2NR_2$, and $X^3$ is OR. Preferably, $X^2$ and $X^3$ are forming a five- or six-membered heterocycle.

More preferably, the polyethylene glycol substituted acyl borate of the third preferred embodiment is selected from the group consisting of (XII) to (XV)

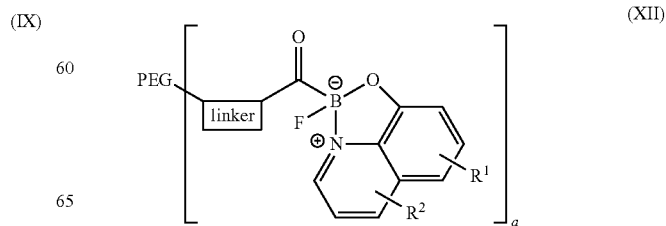

-continued

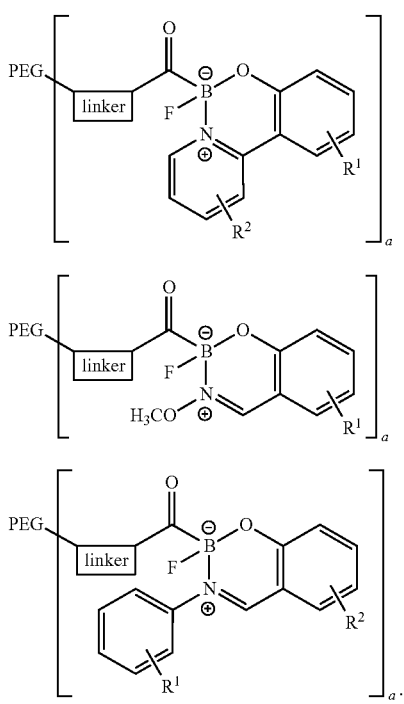
(XIII)

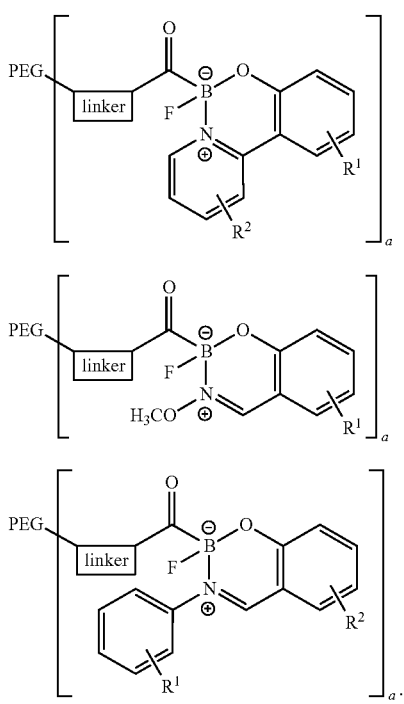
(XIV)

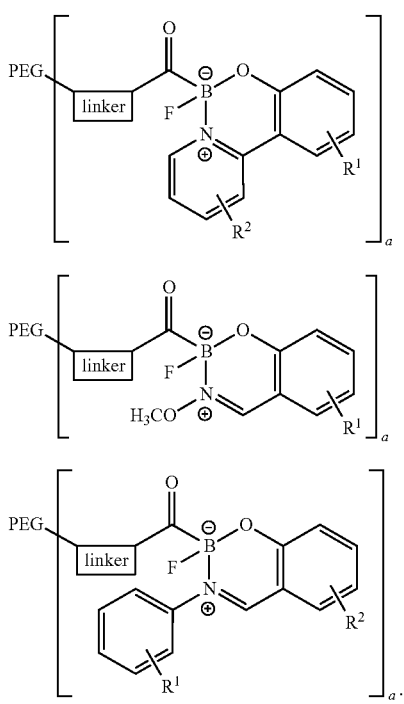
(XV)

In compounds (XII) to (XV), $R^1$ and $R^2$ are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl. More preferably, $R^1$ and $R^2$ are independently of one another selected from the group consisting of hydrogen, $C_1$-$C_8$ alkyl, $C_1$-$C_8$ alkoxy, halogen, $C_1$-$C_8$ alkenyl, $C_1$-$C_8$ alkynyl, nitrile, nitro, $C_1$-$C_8$ aliphatic ester, amide, and $C_1$-$C_8$ thioalkyl. Most preferably, $R^1$ and $R^2$ are independently of one another selected from the group consisting of hydrogen, $C_1$-$C_4$ alkyl, $C_1$-$C_4$ alkoxy, halogen, $C_1$-$C_4$ alkenyl, $C_1$-$C_4$ alkynyl, nitrile, nitro, $C_1$-$C_4$ aliphatic ester, amide, and $C_1$-$C_4$ thioalkyl. In one particularly preferred embodiment, $R^1$ and $R^2$ are hydrogen, and in another particularly preferred embodiment, $R^1$ is hydrogen and $R^2$ is methyl.

Preferably, the polyethylene glycol substituted acyl borate of the third preferred embodiment is of formula (XIII) or (XV), with $R^1$ and $R^2$ preferably being hydrogen or with $R^1$ being hydrogen and $R^2$ being methyl. It has been found that a wide variety of substituents on the aryl or pyridine rings are possible. Also, these compounds have been found to work well in the ligation reaction.

The most reactive compound of the third preferred embodiment is (XIIIb),

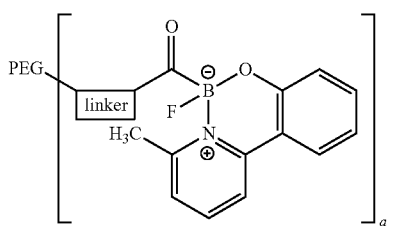
(XIIIb)

with a preferably being 1.

According to a fourth preferred embodiment, $X^1$ and $X^2$ are OR, and $X^3$ is selected from the group consisting of $N^+R_3$, $N^+R_2OR$, $N^+R_2SR$, and $N^+R_2NR_2$. Preferably, $X^1$, $X^2$ and $X^3$ are forming a bicyclic structure.

More preferably, the polyethylene glycol substituted acyl borate of the fourth preferred embodiment is selected from the group consisting of (XVI) to (XXXI)

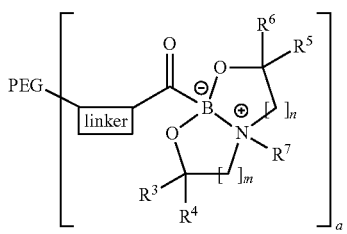
(XVI)

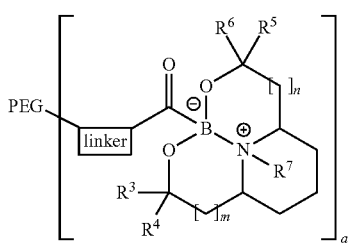
(XVII)

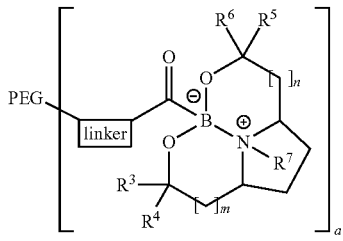
(XVIII)

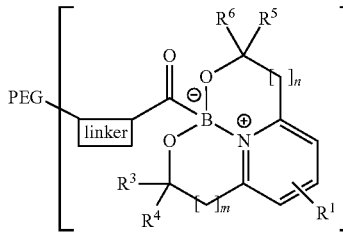
(XIX)

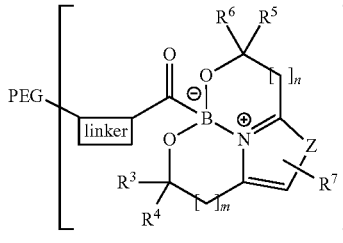
(XX)

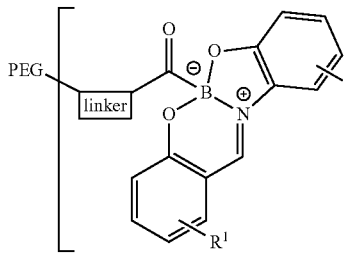
(XXI)

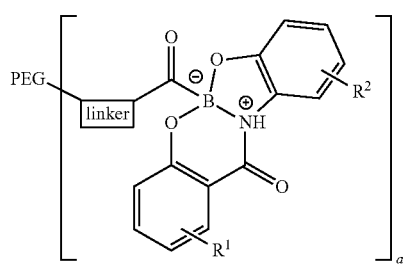

(XXII)

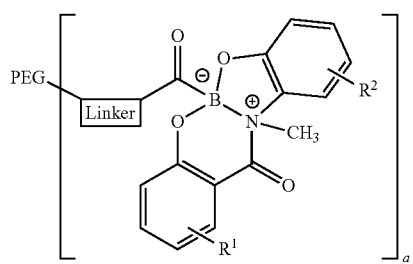

(XXIII)

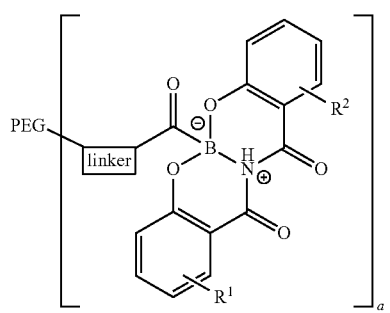

(XXIV)

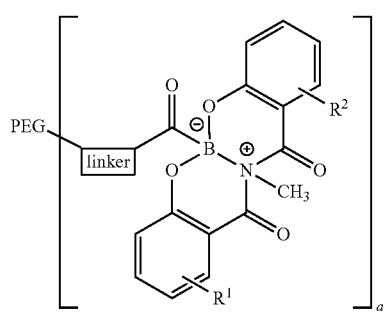

(XXV)

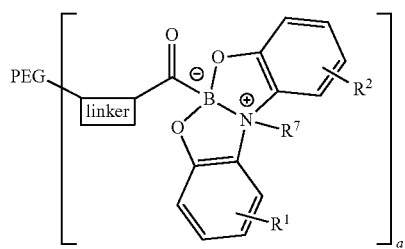

(XXVI)

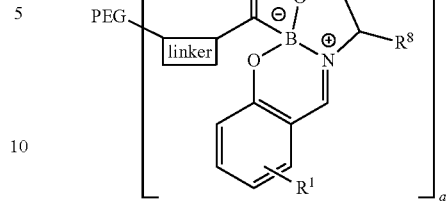

(XXVII)

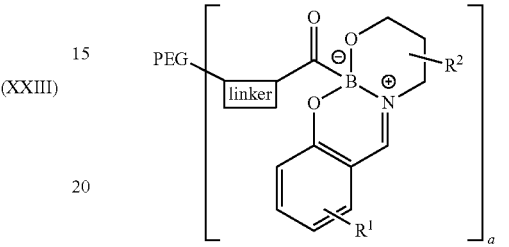

(XXVIII)

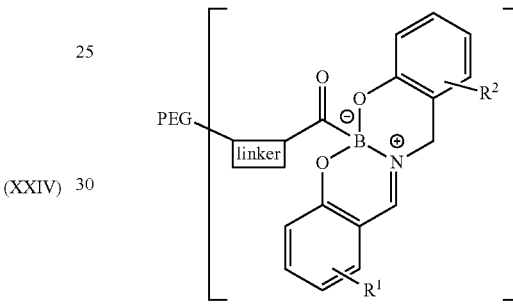

(XXIX)

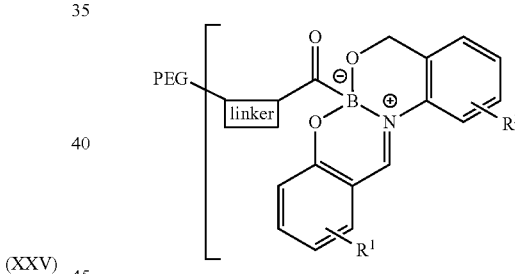

(XXX)

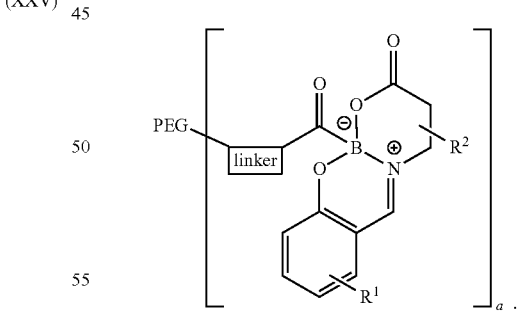

(XXXI)

In compounds (XVI) to (XXXI), $R^1$ and $R^2$ are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl. More preferably, $R^1$ and $R^2$ are independently of one another selected from the group consisting of hydrogen, $C_1$-$C_8$ alkyl, $C_1$-$C_8$ alkoxy, halogen, $C_1$-$C_8$ alkenyl, $C_1$-$C_8$ alkynyl, nitrile, nitro, $C_1$-$C_8$ aliphatic ester, amide, and $C_1$-$C_8$ thioalkyl. Most preferably, $R^1$ and $R^2$ are independently of one another selected from the group consisting of hydrogen, $C_1$-$C_4$ alkyl, $C_1$-$C_4$ alkoxy, halogen, $C_1$-$C_4$ alkenyl, $C_1$-$C_4$ alkynyl, nitrile, nitro, $C_1$-$C_4$ aliphatic ester, amide, and $C_1$-$C_4$ thioalkyl. In a particularly preferred embodiment, $R^1$ and $R^2$ are hydrogen.

Furthermore, $R^3$, $R^4$, $R^5$, and $R^6$ are independently of one another selected from the group consisting of hydrogen, methyl, phenyl, and two geminal substituents forming a carbonyl; $R^7$ is selected from the group consisting of hydrogen, methyl, benzyl, phenyl, and substituted phenyl; $R^8$ is selected from the group consisting of hydrogen, methyl, iso-propyl, benzyl, tert-butyl, sec-butyl, iso-butyl, and substituted phenyl; Z is selected from the group consisting of O, S, NH and $NCH_3$; and m and n are independently of one another selected from the group consisting of 0, 1, 2, and 3.

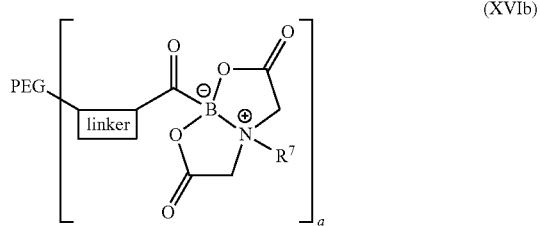
(XVIb)

Preferably, the polyethylene glycol substituted acyl borate of the fourth preferred embodiment is of formula (XVIb), with $R^3/R^4$ and $R^5/R^6$ forming a carbonyl, and m and n being 1. Preferably, a is 1. Particularly preferably, $R^7$ is an alkyl group. It has been found that these compounds work particularly well in the ligation reaction.

According to a fifth preferred embodiment, $X^1$, $X^2$ and $X^3$ are OR. Preferably, $X^1$, $X^2$ and $X^3$ are forming a bicyclic structure.

More preferably, the polyethylene glycol substituted acyl borate of the fifth preferred embodiment is selected from the group consisting of (XXXII) to (XXXIV)

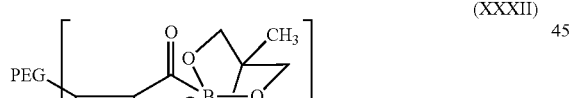
(XXXII)

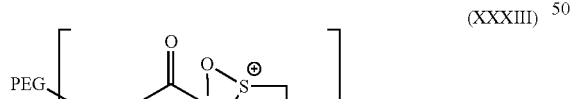
(XXXIII)

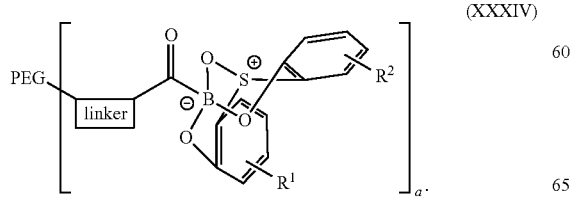
(XXXIV)

In compounds (XXXII) to (XXXIV), $R^1$ and $R^2$ are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl. More preferably, $R^1$ and $R^2$ are independently of one another selected from the group consisting of hydrogen, $C_1$-$C_8$ alkyl, $C_1$-$C_8$ alkoxy, halogen, $C_1$-$C_8$ alkenyl, $C_1$-$C_8$ alkynyl, nitrile, nitro, $C_1$-$C_8$ aliphatic ester, amide, and $C_1$-$C_8$ thioalkyl. Most preferably, $R^1$ and $R^2$ are independently of one another selected from the group consisting of hydrogen, $C_1$-$C_4$ alkyl, $C_1$-$C_4$ alkoxy, halogen, $C_1$-$C_4$ alkenyl, $C_1$-$C_4$ alkynyl, nitrile, nitro, $C_1$-$C_4$ aliphatic ester, amide, and $C_1$-$C_4$ thioalkyl. In a particularly preferred embodiment, $R^1$ and $R^2$ are hydrogen.

Most preferred acyl borates are those where $X^1=X^2=X^3=F$ and those of general formulas (XIII), (XV), (XVIb), and (XVI), in descending order.

According to a preferred embodiment, which more preferably also fulfills the criteria of one of the above first, second, third, fourth or fifth preferred embodiment, the polyethylene glycol substituted acyl borate of the present invention is selected from the group consisting of (XXXV) to (LV)

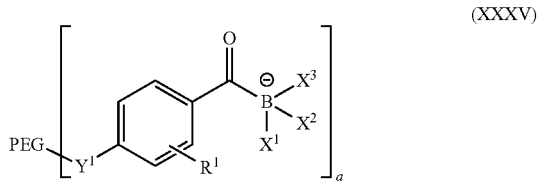
(XXXV)

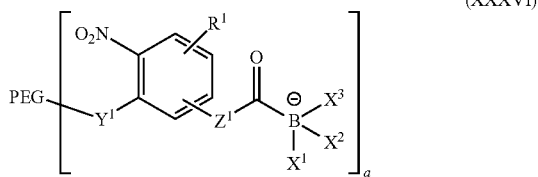
(XXXVI)

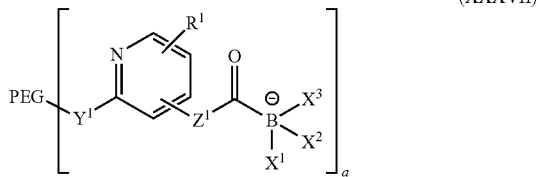
(XXXVII)

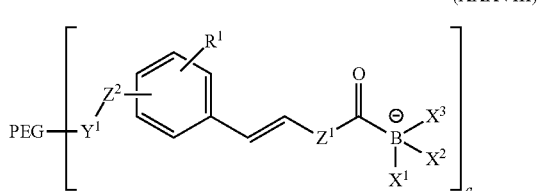
(XXXVIII)

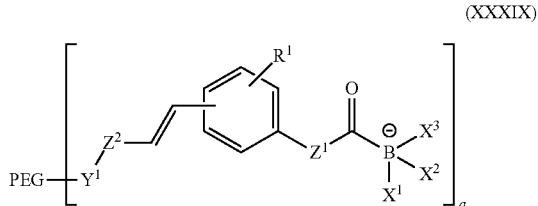
(XXXIX)

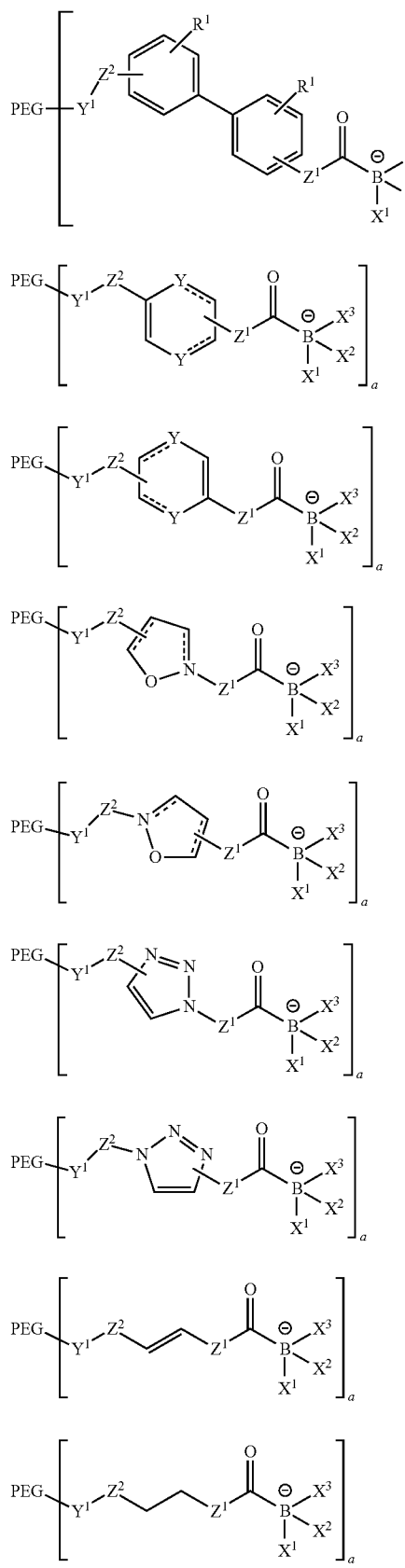
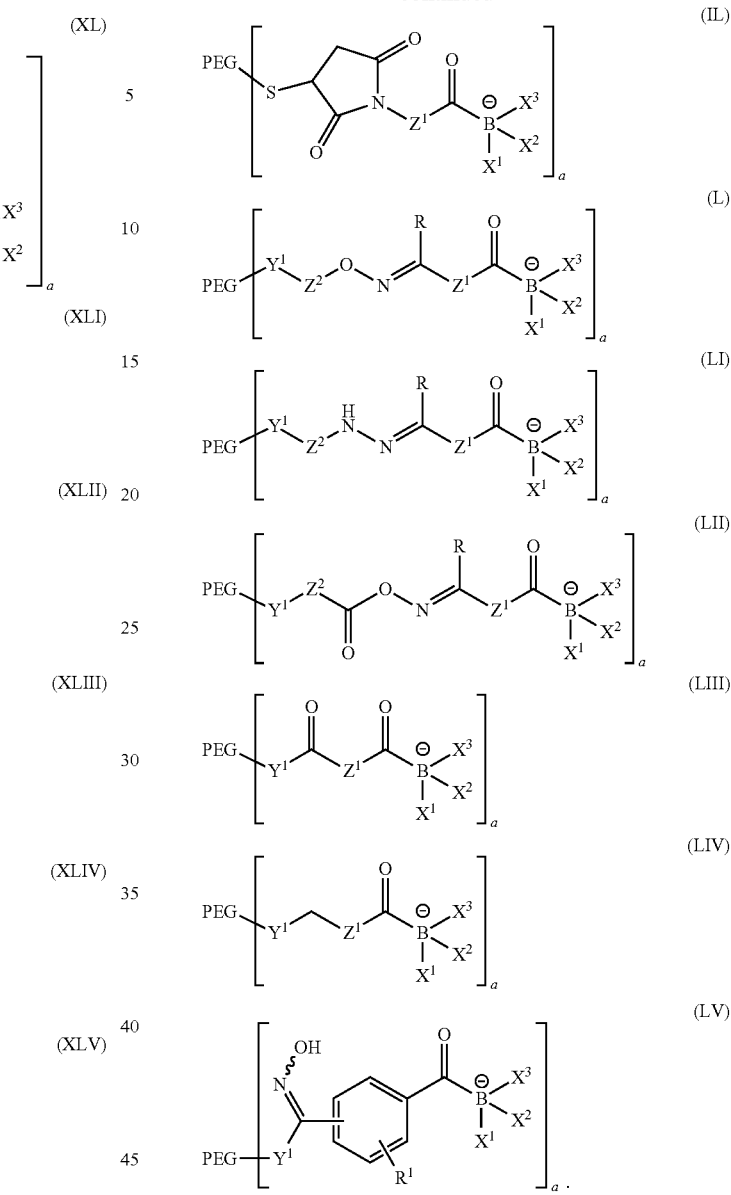

In compounds (XXXV) to (LV), Y is selected from the group consisting of CH, $CR^1$, O, and $NR^9$; $Y^1$ is selected from the group consisting of O, S, NH, alkylamino, and cyclo-alkylamino; $Z^1$ and $Z^2$ are independently of one another selected from the group consisting of $C_1$-$C_8$ alkyl, aryl, substituted aryl, $C_1$-$C_8$ alkoxy, $C_1$-$C_8$ thioalkyl, $C_1$-$C_8$ alkyl amide, and aromatic amide, whereby the term "$C_1$-$C_8$ alkoxy" also includes short polyethylene glycol chains having 1 to 8 C atoms; $R^1$ is selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl; and $R^9$ is selected from the group consisting of $C_1$-$C_{16}$ alkyl, acyl, formyl, carbamoyl, aliphatic sulfonyl, and aromatic sulfonyl.

More preferably, $R^1$ is selected from the group consisting of hydrogen, $C_1$-$C_8$ alkyl, $C_1$-$C_8$ alkoxy, halogen, $C_1$-$C_8$ alkenyl, $C_1$-$C_8$ alkynyl, nitrile, nitro, $C_1$-$C_8$ aliphatic ester, amide, and $C_1$-$C_8$ thioalkyl. Most preferably, $R^1$ is selected from the group consisting of hydrogen, $C_1$-$C_4$ alkyl, $C_1$-$C_4$ alkoxy, halogen, $C_1$-$C_4$ alkenyl, $C_1$-$C_4$ alkynyl, nitrile, nitro, $C_1$-$C_4$ aliphatic ester, amide, and $C_1$-$C_4$ thioalkyl.

In a particularly preferred embodiment, the polyethylene glycol substituted acyl borate of the present invention is of formula (XXXV), with $Y^1$ being O, $R^1$ being H, a being 1, and $X^1$, $X^2$ and $X^3$ being F.

According to a preferred embodiment, the polyethylene glycol substituent (denoted as "PEG" in the formulas) is a linear or branched polyethylene glycol substituent of up to 200 kDa, which is optionally substituted with one or more functional groups selected from the group consisting of hydroxyl, carboxylic acid, carboxylic acid ester, amine, thiol, carbonate, carbamate, azide, alkyne, hydroxylamine, hydrazine, aldehyde, ketone, maleimide, and halogen. The polyethylene glycol substituent is preferably functionalized at one or both termini as activated ester, ketone, aldehyde, maleimide or by a tag, such as biotin. Preferably, PEG is a polyethylene glycol substituent of about 750 Da to about 80 kDa.

In a further aspect, the present invention also refers to a method for the preparation of polyethylene glycol substituted acyl borates of the general formula (I), and in particular of those of the above described preferred embodiments.

In general, such a polyethylene glycol substituted acyl borate may be prepared by preparing the corresponding polyethylene glycol substituted alkyl halide or aldehyde or a compound easily converted to such an aldehyde, e.g. the corresponding alcohol, carboxylic acid or carboxylic acid ester, and then converting said aldehyde to the corresponding acyl borate according to the method described in Dumas, A. M.; Bode, J. W. "Synthesis of Acyltrifluoroborates", *Org. Lett.* 2012, 14, 2138-2141.

Alternatively, it is also possible to prepare a polyethylene glycol substituted acyl borate of the general formula (I) by coupling a suitably functionalized PEG moiety to a suitably functionalized acyl borate, thereby forming the linker group.

In particular, depending on the desired linker group, such a polyethylene glycol substituted acyl borate may be prepared by a nucleophilic aromatic substitution reaction, a metal catalyzed cross-coupling reaction, a cycloaddition reaction, an olefin metathesis reaction, a thiol-maleimide addition reaction, an oxime or hydrazine coupling reaction, or a nucleophilic addition reaction, for instance.

In a first preferred embodiment, the polyethylene glycol substituted acyl borate of the present invention is prepared by nucleophilic aromatic substitution. This affords a polyethylene glycol substituted acyl borate, the linker group of which comprises an aromatic or heteroaromatic moiety, optionally comprising further substituents or intermediate groups. Suitable aromatic or heteroaromatic moieties include, but are not limited to, phenyl groups, pyridyl groups, oxazole groups, thiazole groups, isoxazole groups, triazole groups, pyrazine groups or other electron deficient heteroaromatic groups, all of which may be substituted or non-substituted.

In general, the polyethylene glycol substituent and the acyl borate unit may be arranged on said aromatic or heteroaromatic moiety in any relative arrangement, i.e. in ortho-, meta- or para-arrangement. Optionally, an intermediate group may be arranged between the aromatic or heteroaromatic moiety and the PEG/acyl borate, respectively. Alternatively or in addition, there may be also one or more other substituents on the aromatic or heteroaromatic moiety.

Preferably, a polyethylene glycol substituted acyl borate of formula (XXXV), (XXXVI) or (XXXVII) is prepared by said nucleophilic aromatic substitution, in particular by reacting an aryl fluoride with an alcohol.

In a second preferred embodiment, the polyethylene glycol substituted acyl borate of the present invention is prepared by a metal catalyzed cross-coupling reaction. These cross-coupling reactions are well known in the field and generally afford a carbon-carbon bond between two $sp^2$-carbons. Typical products include vinyl substituted aromatic (e.g. phenyl) or heteroaromatic (e.g. pyridyl) compounds and biaromatic compounds, wherein the latter may also comprise one or two heteroaromatic moieties.

Nowadays, the most important and most frequently used cross-coupling reactions involve a palladium, platinum, nickel or copper catalyst. Preferably, the polyethylene glycol substituted acyl borate of the present invention is prepared by a Suzuki-, Stille-, Hiyama- or Heck-type cross-coupling reaction.

Preferably, a polyethylene glycol substituted acyl borate of formula (XXXVIII), (XXXIX) or (XL) is prepared by said metal catalyzed cross-coupling reaction.

In a third preferred embodiment, the polyethylene glycol substituted acyl borate of the present invention is prepared by a [4+2] or a [3+2] cycloaddition reaction. These cycloaddition reactions are well known in the field and are usually conducted at elevated temperature. [4+2] cycloaddition reactions typically afford cyclohexenes, dihydropyrans or tetrahydropyridines, and [3+2] cycloaddition reactions typically afford tetrahydrofuranes, isoxazolidines, isoxazolines, pyrrolidines, pyrrolines, pyrazoles or triazoles.

The most common [4+2] or a [3+2] cycloaddition reactions are nowadays Diels-Alder reactions, hetero-Diels-Alder reactions, and 1,3-dipolar cycloadditions, which are therefore particularly preferred for the preparation of the polyethylene glycol substituted acyl borate of the present invention.

Preferably, a polyethylene glycol substituted acyl borate of one of formulas (XLI) to (XLVI) is prepared by said [4+2] or [3+2] cycloaddition reaction.

In a fourth preferred embodiment, the polyethylene glycol substituted acyl borate of the present invention is prepared by an olefin metathesis reaction. These reactions are generally catalyzed by metal complexes. Modern catalysts are well-defined organometallic compounds that come in two main categories, commonly known as Schrock catalysts and Grubbs' catalysts. Schrock catalysts are molybdenum(IV)- and tungsten(IV)-based, whereas Grubbs' catalysts, on the other hand, are ruthenium(II) carbenoid complexes. Grubbs' catalysts are often modified with a chelating isopropoxystyrene ligand to form the related Hoveyda-Grubbs catalyst.

An olefin metathesis reaction will generally form a carbon-carbon double bond. In the present case, said carbon-carbon double bond will be arranged between the polyethylene glycol and the acyl borate moiety. However, said carbon-carbon double bond may optionally also be reduced to a carbon-carbon single bond subsequently, such that the final polyethylene glycol substituted acyl borate does not necessarily contain a carbon-carbon double bond.

Preferably, a polyethylene glycol substituted acyl borate of formula (XLVII) or (XLVIII) is prepared by said olefin metathesis reaction.

In a fifth preferred embodiment, the polyethylene glycol substituted acyl borate of the present invention is prepared by a thiol-maleimide addition reaction. In this reaction, a thiol undergoes a 1,4-type addition to a maleimide, leading to the formation of a thioether linkage.

Preferably, a polyethylene glycol substituted acyl borate of formula (IL) is prepared by said thiol-maleimide addition reaction.

In a sixth preferred embodiment, the polyethylene glycol substituted acyl borate of the present invention is prepared by an oxime or hydrazine coupling reaction. Preferred starting materials include aldehydes or ketones on the one hand and O-substituted hydroxylamines or hydrazines on the other hand. This reaction is well known in the field and will typically proceed with high chemoselectivity. The reaction is typically conducted under aqueous acidic buffer, optionally in the presence of a nucleophilic additive, such as aniline.

Preferably, a polyethylene glycol substituted acyl borate of formula (L), (LI) or (LII) is prepared by said oxime or hydrazine coupling reaction.

In a seventh preferred embodiment, the polyethylene glycol substituted acyl borate of the present invention is prepared by a nucleophilic addition reaction, preferably to an activated ester.

Preferably, a polyethylene glycol substituted acyl borate of formula (LIII), (LIV) or (LV) is prepared by said nucleophilic addition reaction.

In a further aspect, the present invention also refers to a method for the preparation of a polyethylene glycol substituted macromolecule. According to this method, a polyethylene glycol substituted acyl borate of formula (I) is reacted with a hydroxylamine moiety present in the macromolecule to form an amide bond. Thus, said reaction is an amide-forming ligation.

The macromolecule is preferably selected from the group consisting of synthetic, isolated, expressed or modified peptides, synthetic, isolated, expressed or modified proteins, DNA, and RNA.

The reaction between the hydroxylamine-bearing macromolecule and the polyethylene glycol substituted acyl borate is preferably conducted under aqueous conditions. Suitable solvent mixtures are, for instance, THF/$H_2O$, $CH_3CN$/$H_2O$, tBuOH/$H_2O$, DMSO/tBuOH/$H_2O$. In general, ratios of 7:3 to 3:7 have been found to be advantageous. Best results have so far been observed for a 1:1 mixture of tBuOH/$H_2O$.

Preferably, the amide-forming ligation reaction is performed under acidic conditions, more preferably at a pH of less than 4, and in particular at a pH of about 1. The pH is preferably adjusted by the addition of acid, more preferably by the addition of HCl, TFA, oxalic acid, AcOH and/or $H_3PO_4$.

Preferably, the amide-forming ligation reaction is preferably conducted at room temperature or slightly elevated temperature. Suitable reaction temperatures range from about −20° C. to about 160° C., with a temperature of about 10° C. to about 60° C. being preferred. Particularly preferred are reaction temperatures of about 20° C. to about 40° C.

Particularly preferably, the reaction of the polyethylene glycol substituted acyl borate with the macromolecule is performed under acidic conditions in a mixture of tert-butanol and water.

The ligation forming the amide bond generally occurs upon simple mixing the polyethylene glycol substituted acyl borate with the hydroxylamine-bearing macromolecule.

The amide-forming ligation reaction of the present invention is highly chemoselective, such that it may be used for connecting molecules bearing a variety of unprotected functional groups. Furthermore, the reaction also proceeds extremely fast: A second order rate constant of >20 $M^{-1}s^{-1}$ has been measured. Consequently, these reactions enable selective conjugations of large molecules at micromolar concentrations using equimolar amounts of reactants.

In a preferred embodiment, the polyethylene glycol substituted macromolecule is prepared by reacting one of the above described preferred polyethylene glycol substituted acyl borates—i.e. an acyl trifluoroborate or an acyl borate of one of formulas (II) to (LV)—with the hydroxylamine-bearing macromolecule.

Thanks to the amide-forming ligation being so highly chemoselective, the macromolecule may comprise one or more unprotected functional groups other than the hydroxylamine required for the ligation, without the risk of undesired side reactions.

In particular, the macromolecule may comprise one or more unprotected functional groups selected from the group consisting of carboxylic acid, hydroxyl, phenol, thiol, amine, ammonium, guanidine, guanidinium, imidazole, indole, and methylthio ether. It has been found that none of these functional groups will undergo a reaction with the acyl borate under the above described reaction conditions.

In a preferred embodiment, the hydroxylamine moiety is present at the N-terminus of the peptide or protein, at the 3'- or the 5'-end of the DNA or RNA, or on a side chain of the peptide or protein, in the latter case preferably on a lysine- or ornithine-derived side chain. Lysine- or ornithine-derived side chains are preferred because these may be incorporated into expressed proteins. However, also other attachments are acceptable.

Preferably, the ligation reaction is performed with an acyl trifluoroborate, i.e. where $X^1=X^2=X^2=F$, of the present invention.

In a further aspect, the present invention also refers to a polyethylene glycol substituted macromolecule obtainable by the method according to the present invention.

Preferably, said macromolecule comprises a peptide, macrocyclic peptide, protein (including antibodies), RNA, and/or DNA.

The present invention is further illustrated by means of the following examples, which are not restrictive in any way:

General Methods

Unless otherwise noted, all reactions were carried out in oven-dried glassware sealed with rubber septa under an atmosphere of dry $N_2$ and were stirred with Teflon-coated magnetic stir bars. Thin layer chromatography (TLC) was performed on Merck TLC plates (0.25 mm) pre-coated with silica gel 60 F254 and visualized by UV quenching and staining with $KMnO_4$ or ninhydrin solution. Flash column chromatography was performed under a forced-flow of air using Silicycle SiliaFlash F60 (40-63 μm particle size). Peptides were purified by high performance liquid chromatography (HPLC) on Jasco analytical and preparative instruments with dual pumps, mixer and degasser, a variable wavelength UV detector and a Rheodyne 7725i injector fitted with a 20 to 1000 μL sample loop. The mobile phase for analytical and preparative HPLC were Millipore-$H_2O$ with 0.1% TFA (Buffer A) and HPLC grade MeCN with 0.1% TFA (Buffer B). The eluent was monitored simultaneously at 220 nm, 254 nm and 301 nm. Flow rates for analytical (4.6×250 mm) and preparative (20×250 mm) HPLC were 1 ml and 10 ml respectively. NMR spectra were recorded on a Bruker AV-300, a Bruker AV-400, a Bruker AV-III-500 or a Bruker DRX-II-500. All chemical shifts (δ) are reported in ppm relative to residual solvent peaks. Data for $^1$H NMR are reported as follows: chemical shift (multiplicity, coupling constants where applicable, number of hydrogens). Abbreviations are as follows: s (singlet), d (doublet), t (triplet), q (quartet), dd (doublet of doublet), dt (doublet of triplet), ddt (doublet of doublet of triplet), m (multiplet), br (broad). In $^{19}$F NMR, trifluoroborate multiplets are reportet as the average of the observed signals. IR spectra were recorded on a Jasco FT/IR-4100 spectrometer and only major peaks are reported in frequency of absorption (cm$^{-1}$). Melting points were measured on an Electrothermal Mel-Temp melting point apparatus using open glass capillaries and are uncorrected. Optical rotations were measured on a Jasco P-1010 operating at the sodium D line with a 100 mm path length cell. LCMS analysis was performed on a Dionex UltiMate 3000 RSLC connected to a Surveyor MSQ Plus mass spectrometer; a reversed-phase RESTEK Pinnacle II C18 (4.6×50 mm) column was used, running a gradient of 5 to 100% $CH_3CN$ in $H_2O$ over 6.5 min, 100% $CH_3CN$ for 2.5 min. High-resolution mass spectra were obtained by the mass spectrometry service of the ETH Zurich Laboratorium für Organische Chemie on a Varian IonSpec FT-ICR (ESI), a Bruker Daltonics maXis ESI-QTOF spectrometer (ESI), or a Bruker Daltonics SOLARIX spectrometer (MALDI). MALDI spectra of PEGylated peptide 16a and 16c were obtained by Protein Analysis Group, Functional Genomics Center Zurich.

Solvents and Reagents

All organic solvents (tBuOH, $CH_3OH$, DMF, THF, $CH_2Cl_2$, $CH_3CN$, DMSO) were used as supplied (ACS or HPLC grade) unless otherwise noted. THF was purified by distillation from sodium benzophenone ketyl prior to use. $CH_2Cl_2$ was purified by distillation from $CaH_2$. Dry DMSO was purchased from Acros. $H_2O$ used for preparing 1:1 tBuOH/$H_2O$ was obtained from a Millipore purification system. $Et_3N$ and $iPr_2NEt$ were purified by distillation from $CaH_2$. Starting materials were used as supplied by commercial vendors or prepared by the method described in the corresponding reference.

Solid phase peptide synthesis (SPPS): All peptide segments were synthesized on a CS Bio 136X peptide synthesizer using Fmoc SPPS chemistry. An inline UV detector was used for monitoring Fmoc deprotection. The following Fmoc amino acids with side-chain protection groups were used: Fmoc-Ala-OH, Fmoc-Arg(Pbf)-OH, Fmoc-Asp(OtBu)-OH, Fmoc-Gln(Trt)-OH, Fmoc-Glu(OtBu)-OH, Fmoc-Gly-OH, Fmoc-His(1-Trt)-OH, Fmoc-Ile-OH, Fmoc-Leu-OH, Fmoc-Lys(Boc)-OH, Fmoc-Phe-OH, Fmoc-Ser(tBu)-OH, Fmoc-Thr(tBu)-OH, Fmoc-Trp(Boc)-OH, Fmoc-Tyr(tBu)-OH, Fmoc-Val-OH. Fmoc deprotections were performed with 20% piperidine in DMF (2×8 min) and monitored by UV at 304 nm with a feedback loop to ensure complete Fmoc removal. Couplings were performed with Fmoc-amino acid (4.0 equiv to resin substitution), HCTU (3.9 equiv) and $iPr_2NEt$ (6.0 equiv) in DMF. After pre-activating for 3 min, the solution was transferred and allowed to react with the peptide on-resin for either 45 min or 75 min depending on the amino acid. After coupling, the resin was treated with 20% acetic anhydride in DMF for capping any unreacted free amine.

EXAMPLE 1

Synthesis of Acyl Trifluoroborates for PEGylation

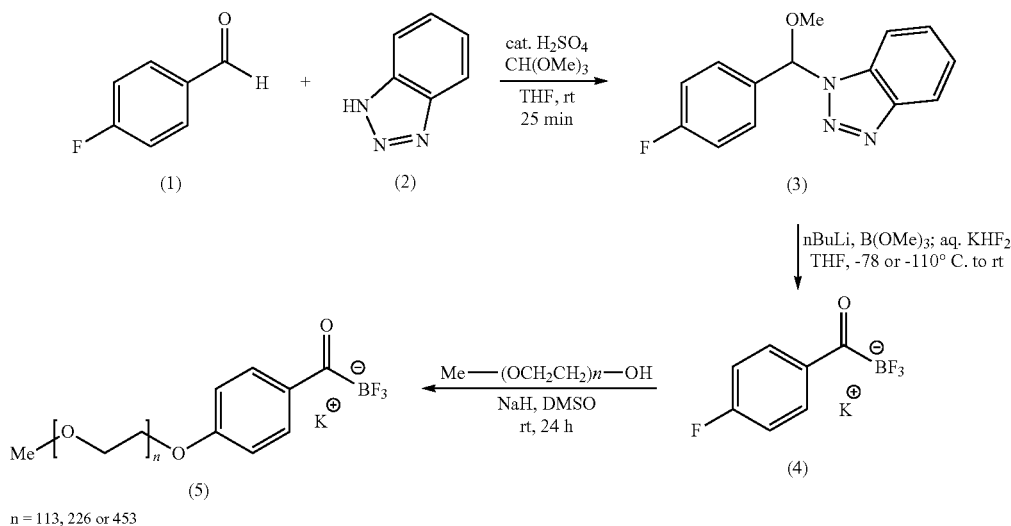

1-(Methoxy(4-fluorophenyl)methyl)-1H-benzotriazole 3

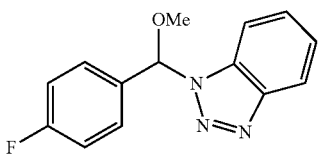

4-Fluorobenzaldehyde 1 (5.00 g, 40.3 mmol, 1.0 equiv), benzotriazole 2 (4.80 g, 40.3 mmol, 1.0 equiv), MeOH (3.26 ml, 80.6 mmol, 2.0 equiv), and trimethylorthoformate (13.2 ml, 120.9 mmol, 3.0 equiv) were dissolved quickly in dry THF (60 ml) at room temperature. To this solution was added $H_2SO_4$ (12 drops), resulting in a white precipitate. The reaction was stirred at room temperature for 25 minutes, 1.0 g solid $NaHCO_3$ was added and the heterogeneous solution was concentrated. The resulting oil was dissolved in $CH_2Cl_2$ (20 ml), filtered, concentrated and dried at high vacuum. The purity of acetal 3 (10.3 g, 99% yield) was better than 95% and it was used without further purification.

Colorless oil; IR (thin film) 3070, 2937, 2834, 1606, 1509, 1226, 1092, 927 $cm^{-1}$; $^1$H NMR (400 MHz, $CDCl_3$) 8.12-8.07 (m, 1H), 7.45-7.39 (m, 1H), 7.39-7.31 (m, 1H), 7.27-7.23 (m, 1H), 7.09 (s, 1H), 7.08-7.02 (m, 1H), 3.45 (s, 3H); $^{13}$C NMR (100 MHz, $CDCl_3$) 163.00 (d, J=248.4 Hz, CF), 147.06 (C), 131.99 (C), 130.91 (C), 127.87 (d, J=8.4 Hz, 2CH), 127.67 (CH), 124.40 (CH), 120.06 (CH), 115.63 (d, J=21.8 Hz, 2CH), 111.44 (CH), 56.90 ($CH_3$); $^{19}$F NMR (377 MHz, $CDCl_3$) −112.36 (s); HRMS (ESI) calc'd for $C_{14}H_{12}FN$ NaO [M+Na]+: 280.0857, found: 280.0854.

Potassium 4-fluorobenzoyltrifluoroborate 4

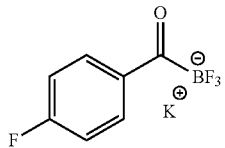

(4)

In a 500 ml flask, acetal 3 (10.0 g, 38.9 mmol, 1.05 equiv) was dissolved in dry THF (250 ml) at RT. The flask was placed in a dry ice/EtOH bath which was cooled with liq. $N_2$ until solidification of EtOH (ca. −110° C.) and stirred for at least 15 minutes. nBuLi (1.6 M in hexane, 23 ml, 37.0 mmol, 1.0 equiv) was added slowly down the side of the flask over 6 min. During this time, an intense green color developed. The solution was stirred for 2 min following the end of nBuLi addition, and neat $B(OMe)_3$ (8.25 ml, 74.0 mmol, 2.0 equiv) was added gradually over 1 min directly into the solution. The deep green color gradually became red after 5 to 10 minutes of stirring. The flask was kept in the dry ice/EtOH bath for 1 h, which slowly warmed to −78° C., and then removed from the bath and, with vigorous stirring, five portions of sat aq. $KHF_2$ were added (20 ml per minute, 100 ml total). As the reaction warmed, a biphasic mixture consisting of a milky white aqueous layer and a yellow organic layer formed. This was stirred overnight (~12 hours from the time of $KHF_2$ addition) over which time the organic layer stayed yellow. The two layers were separated and the yellow organic phase was concentrated using a rotary evaporator until some water remained. This yellow wet slurry was mixed with 40 ml $Et_2O$. Filtration, washing with additional $Et_2O$ (4×30 ml), and drying under high vacuum gave the product as a white solid (5.34 g, 63% yield). (Instead of dry ice/ethanol/liq. $N_2$ bath (at −110° C.) also dry ice/aceton bath (at −78° C.) is suitable, but the yield drops to 40%.)

White solid; m.p. 257° C. (decomp.); IR (neat) 3013, 1637, 1580 $cm^{-1}$; $^1$H NMR (500 MHz, acetone-$d_6$) 8.17-8.11 (m, 2H), 7.15-7.09 (m, 2H); $^{13}$C NMR (151 MHz, DMSO-dd 235.59-232.05 (m, CO), 165.45 (d, J=248.4 Hz, CF), 138.95 (d, J=12.0 Hz, C), 131.83 (dd, J=8.8, 1.8 Hz, 2CH), 115.23 (d, J=21.4 Hz, 2CH); $^{19}$F NMR (471 MHz, acetone-$d_6$) −111.27 (s, 1F), −144.70 (dd, J=102.0, 48.9 Hz, 3F); $^{11}$B NMR (160 MHz, acetone-dd −0.84 (dd, J=104.4, 51.3 Hz); HRMS (ESI$^-$) calc'd for $C_7H_4BF_4O$ [M-K]$^-$: 191.0298, found: 191.0297.

PEGylated Potassium Acyltrifluoroborate 5a

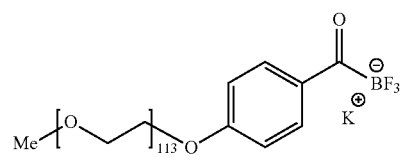

(5a)

Poly(ethylene glycol) methyl ether (Aldrich; ~5000 g/mol, 1.0 g, 0.20 mmol, 1.0 equiv) was dissolved in 50 ml dry toluene at 50° C. and the toluene was evaporated. The azeotropic distillation was repeated three times (3 ×50 ml). The PEG was dried under high vacuum and dissolved in ml dry DMSO (at 50° C.). Sodium hydride (16 mg, 60% in mineral oil, 0.40 mmol, 2.0 equiv) was added to the homogeneous PEG solution at room temperature and stirred for hours. The deprotonated poly(ethylene glycol) methyl ether solution was added to potassium 4-fluorobenzoyl trifluoroborate 4 (0.46 g, 2.0 mmol, 10.0 equiv; dried by azeotropic distillation) and stirred for 24 hours. Conversion was greater than 95% according to NMR spectra of the crude reaction mixture. The reaction mixture was diluted with 8 ml deionized $H_2O$, filled into a dialysis membrane tube (MWCO: 3,500) and placed into 2 l, 6 mM aq KF and stirred for 48 hours. The aqueous solution of potassium fluoride was changed 4 times for a new batch. The product was lyophilized to afford 791 mg (76% yield) of 5a as a white solid.

$^1$H NMR (300 MHz, acetone-$d_6$) 8.17 (d, J=8.7 Hz, 2H), 7.03 (d, J=8.8 Hz, 2H), 4.29-4.22 (m, 2H), 3.90-3.80 (m, 4H), 3.59 (br s, 390H), 3.39-3.32 (m, 2H), 3.29 (s, 3H); $^{13}$C (151 MHz, acetone-$d_6$) 132.4 (2CH), 114.8 (2CH), 72.7 ($CH_2$), 71.3 (195$CH_2$), 70.3 ($CH_2$), 68.6 ($CH_2$), 58.8 ($CH_2$); $^{19}$F NMR (471 MHz, acetone-$d_6$) −142.18 (bs, 3F); $^{11}$B NMR (160 MHz, acetone-$d_6$) −0.9 (bs).

Pegylated Potassium Acyltrifluoroborate 5B

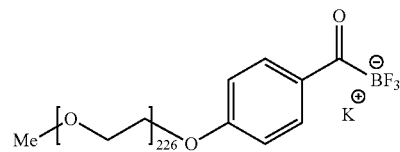

(5b)

Prepared from 1.0 g poly(ethylene glycol) methyl ether (~10,000 g/mol, 0.10 mmol) by the same procedure as 5a. After lyophilization, 848 mg (83% yield) of 5b was obtained as a white solid.

$^1$H NMR (400 MHz, acetone-$d_6$) 8.08 (d, J=8.7 Hz, 2H), 6.88 (d, J=8.9 Hz, 2H), 4.19-4.15 (m, 2H), 3.86-3.81 (m, 2H), 3.59 (br s, 924H), 3.29 (s, 3H); $^{19}$F NMR (377 MHz, acetone-$d_6$) −144.00 (dd, J=91.9, 44.0 Hz, 3F).

PEGylated Potassium Acyltrifluoroborate 5c

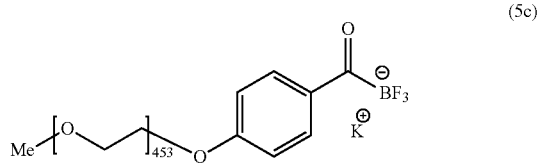

(5c)

Prepared from 1.0 g poly(ethylene glycol) methyl ether (~20,000 g/mol, 0.05 mmol) by the same procedure as 5a. After lyophilization, 806 mg (80% yield) of 5c was obtained as a white solid.

$^1$H NMR (400 MHz, DMSO-$d_6$) 7.87 (d, J=8.6 Hz, 2H), 6.90 (d, J=8.8 Hz, 2H), 4.14-4.09 (m, 2H), 3.78-3.72 (m, 2H), 3.51 (br s, 1773H), 3.24 (s, 3H); $^{19}$F NMR (377 MHz, DMSO-$d_6$) −141.1 (bs, 3F).

EXAMPLE 2

Synthesis of β-Alanine Derivative 10 equiv) and DMAP (430 mg, 3.52 mmol, 0.1 equiv) at room temperature, and the mixture was stirred at 40° C. for 9 hours. After cooling to room temperature, the mixture was diluted with CH$_2$Cl$_2$ and 1M aq. HCl was added. The aqueous phase was extracted with CH$_2$Cl$_2$ (3×). The combined organic phases were washed with brine, dried over Na$_2$SO$_4$, filtered and concentrated under reduced pressure. The crude material was purified by flash chromatography, eluting with hexane/EtOAc to afford 8 as a colorless oil (7.29 g, 94% yield). IR (thin film) 3433, 2089, 1643 cm$^{-1}$; $^1$H NMR (400 MHz, CDCl$_3$) 7.78 (s, 1H), 3.34 (q, J=7.2 Hz, 4H), 1.48 (s, 9H), 1.28-1.11 (m, 6H); NMR (100 MHz, CDCl$_3$) 156.7, 155.7, 82.9, 43.1, 41.6, 28.2, 14.1, 13.4; HRMS (ESI) calc'd for C$_{10}$H$_{20}$N$_2$O$_4$ [M Na]: 255.1315, found: 255.1317.

3-[1-N-(tert-Butoxycarbonyl)-N-(diethylcarbamoyloxy)amino]-propanoic acid methyl ester 9

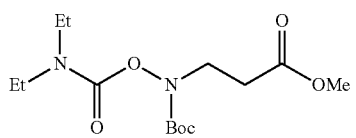

(9)

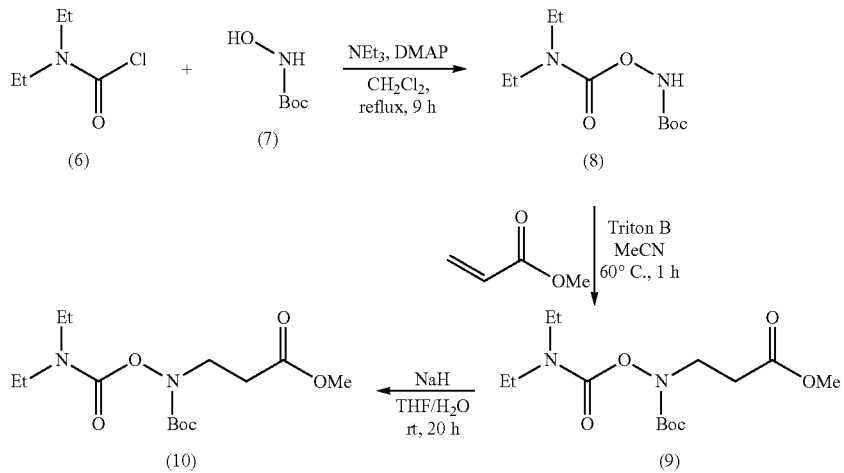

N-tert-Butoxycarbonyl-O-diethylcarbamoylhydroxylamine 8

(8)

To a solution of N-tert-butoxycarbonylhydroxylamine 7 (6.10 g, 45.8 mmol, 1.3 equiv) and Et$_3$N (6.30 ml, 45.8 mmol, 1.3 equiv) in CH$_2$Cl$_2$ (70 ml) were added slowly N,N-diethylcarbamoylchloride 6 (4.60 ml, 35.2 mmol, 1.0

To a solution of methyl acrylate (3.00 ml, 33.6 mmol, 1.5 equiv) and hydroxylamine 8 (5.20 g, 22.3 mmol, 1.0 equiv) in MeCN (22 ml) was added Triton B (1.41 ml, 3.35 mmol, 0.15 equiv, 40% in MeOH) at room temperature, and the mixture was stirred for 2 hours at 60° C. After cooling to room temperature, the solution was concentrated under reduced pressure. The residue was purified by flash column chromatography, eluting with hexane/EtOAc to give 9 as a pale yellow oil (6.18 g, 87% yield).

IR (thin film) 2977, 2937, 1742, 1422, 1367, 1266, 1166, 1142, 1105 cm$^{-1}$; $^1$H NMR (400 MHz, CDCl$_3$) 3.91 (t, J=6.8 Hz, 2H), 3.66 (s, 3H), 3.37-3.20 (m, 4H), 2.63 (t, J=6.8 Hz, 2H), 1.44 (s, 9H), 1.15 (t, J=7.2 Hz, 6H); $^{13}$C NMR (100 MHz, CDCl$_3$) 171.9, 154.7, 154.1, 82.1, 51.8, 46.5, 43.1, 41.7, 32.7, 28.3, 14.2, 13.4; HRMS (ESI) calc'd for C$_{14}$H$_{26}$N$_2$O$_6$ [M+H]$^+$: 319.1864, found: 319.1858.

3-[1-N-(tert-Butoxycarbonyl)-N-(diethylcarbamoyloxy)amino]-propanoic acid 10

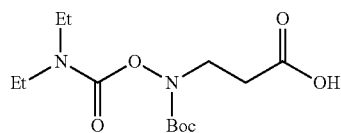

(10)

To a solution of methyl ester 9 (3.90 g, 12.2 mmol, 1.0 equiv) in THF (40.0 ml) was added NaOH (4M in H$_2$O, 9.1 ml, 36.4 mmol, 3.0 equiv). The mixture was stirred for 16 h, then diluted with H$_2$O and EtOAc. The aqueous phase was acidified with 1M aq. HCL and extracted with EtOAc (3×). The combined organic phases were washed with brine, dried over Na$_2$SO$_4$, filtered and concentrated to afford 10 (3.20 g, 86% yield).

Pale yellow oil; IR (thin film) 2978, 2936, 1725, 1425, 1368, 1269, 1166, 1144, 1105 cm$^{-1}$; $^1$H NMR (400 MHz, CDCl$_2$) 3.94 (t, J=6.4 Hz, 2H), 3.38-3.25 (m, 4H), 2.66 (t, J=6.4 Hz, 2H), 1.46 (s, 9H), 1.26-1.10 (m, 6H); $^{13}$C NMR (100 MHz, CDCl$_2$) 175.9, 154.8, 154.6, 82.7, 46.5, 43.3, 41.8, 33.1, 28.3, 14.2, 13.4; HRMS (ESI) calc'd for C$_{23}$H$_{24}$N$_2$O$_6$ [M+Na]: 327.1527, found: 327.1526.

EXAMPLE 3

Synthesis of Peptides 13 (SEQ ID NO 1) and 14 (SEQ ID NO 2)

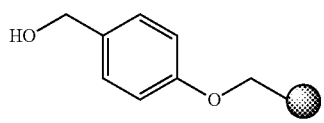

(11)

1.) Fmoc-Gly-OH, DIC
2.) automated SPPS

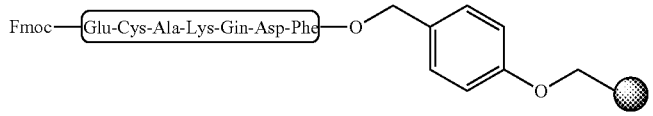

(12)

1.) 20% piperidine, DMF
2.) HCTU, NMM

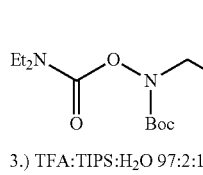

3.) TFA:TIPS:H$_2$O 97:2:1

1.) 20% piperidine, DMF
2.) HCTU, NMM

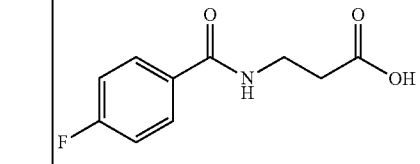

3.) TFA:TIPS:H$_2$O 97:2:1

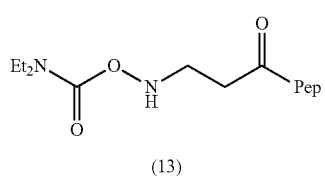

(13)

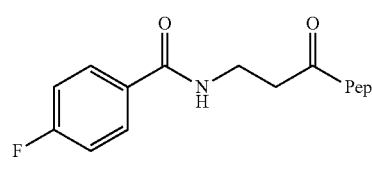

(14)

● = Wang-linker resin

Pep = ⁓⁓⁓―Glu-Cys-Ala-Lys-Gln-Asp-Phe―CO$_2$H

Peptide Hydroxylamine 13 (SEQ ID NO 1; See FIG. 1a):

Peptide hydroxylamine 13 (SEQ ID NO 1) was synthesized on Wang-linker polystyrene resin with a loading capacity of 1.08 mmol/g. The synthesis was performed on 1.09 mmol scale (1.01 g of resin) by the treatment of a solution of Fmoc-Phe-OH (4.27 g, 10.9 mmol, 10.0 equiv to resin) and N,N'-diisopropyl-carbodiimide (843 µl, 5.45 mmol, 5.0 equiv to resin) in $CH_2Cl_2$/DMF for 36 h. The synthesis continued by using automated Fmoc SPPS up to Glu using the procedure described in the general methods section. At this step, 0.67 mmol of resin 12 was separated and the Fmoc group was removed using 20% piperidine in DMF. N-Boc protected carboxylic acid 10 (814 mg, 2.67 mmol, 4.0 equiv to resin) was coupled to the amine using HCTU (1.10 g, 2.67 mmol, 4.0 equiv to resin) and NMM (594 µl, 5.34 mmol, 8.0 equiv to resin) in DMF for 3 h. The resin supported peptide was treated with TFA:TIPS:$H_2O$ (97:2:1) for 3 h and filtered to remove the solid support. Volatiles from the filtrate were evaporated under vacuum. The residue was triturated with MTBE and centrifuged (three cycle repeated) to obtain the crude peptide. Purification was performed by preparative HPLC using Shiseido Capcell Pak C18 column (20×250 mm) with a gradient of 10 to 50% MeCN with 0.1% TFA in 30 min. The product peak eluting at $t_R$=23.2 min was collected and lyophilized to obtain 181 mg of pure 13 (26% yield for synthesis from starting resin, cleavage and purification steps). Analytical HPLC and HRMS were used to confirm the purity and exact mass of the product. m/z calc'd for $C_{43}H_{68}N_{11}O_{16}S$ $[M+H]^+$: 1026.4561, found: 1026.4564.

Figure 2A:
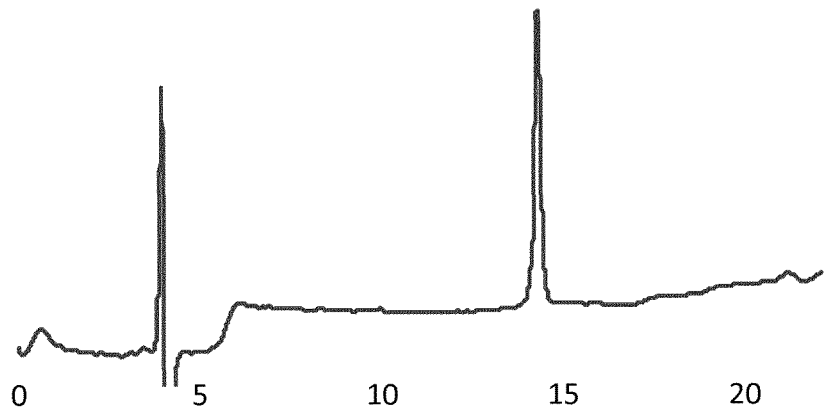
FIG. 2a is a HPLC analysis of purified peptide hydroxylamine 13.
Figure 2B:
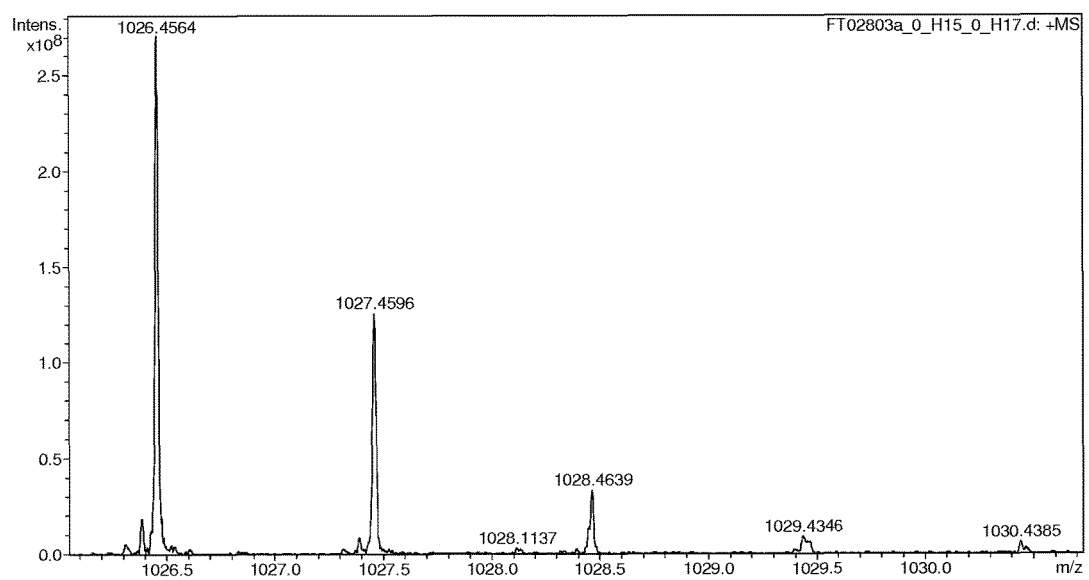
FIG. 2b is a HRMS analysis of purified peptide hydroxylamine 13.

Analytical HPLC of purified 13: See FIG. 2a.
HRMS (MALDI) of purified 13: See FIG. 2b.

Figure 1B:
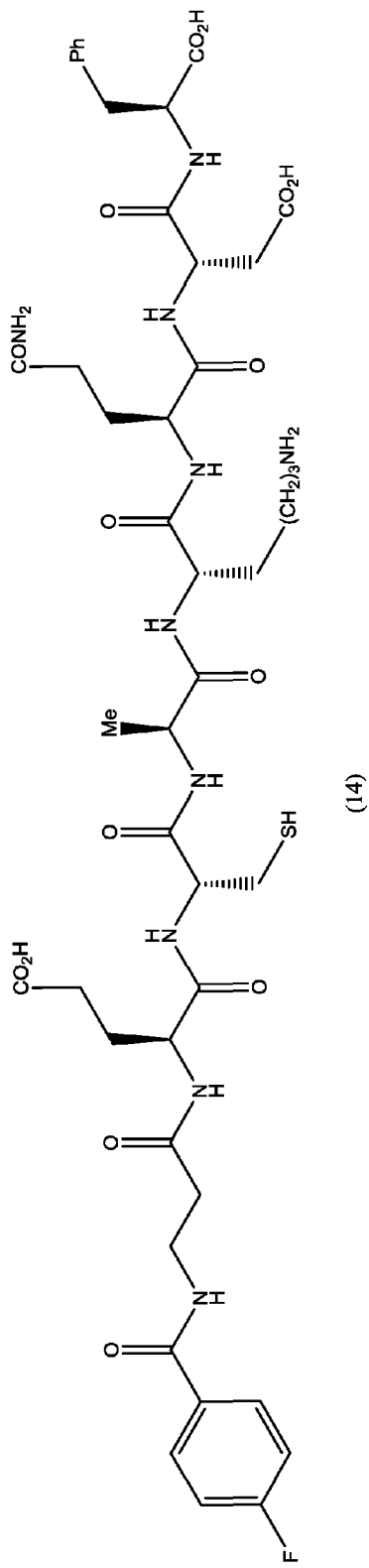
FIG. 1b is a diagram of the chemical structure of a peptide 14 produced by Example 3.

Synthesis of Authentic Sample of Peptide 14 (SEQ ID NO 2; see FIG. 1b):

Peptide 14 (SEQ ID NO 2) was synthesized from 0.196 mmol of resin 12. The Fmoc group was removed using 20% piperidine in DMF and the liberated free amine was coupled with 3-(4-fluorobenzamido)-propanoic acid (165 mg, 0.784 mmol, 4.0 equiv to resin) using HCTU (324 mg, 0.784 mmol, 4.0 equiv to resin) and NMM (174 µl, 1.57 mmol, 8.0 equiv to resin) in DMF for 3 h. The resin supported peptide was treated with TFA:TIPS:$H_2O$ (97:2:1) for 2.5 h and filtered to remove the solid support. Volatiles from the filtrate were evaporated under vacuum. The residue was triturated with MTBE and centrifuged (three cycle repeated) to obtain the crude peptide. Purification was performed by preparative HPLC using Shiseido Capcell Pak C18 column (20×250 mm) with a gradient of 20 to 70% MeCN with 0.1% TFA in 30 min. The product peak eluting at $t_R$=13.5 min was collected and lyophilized to obtain 54.9 mg of pure 14 (27% yield for synthesis from starting resin, cleavage and purification steps). Analytical HPLC and HRMS were used to confirm the purity and exact mass of the product. m/z calc'd for $C_{45}H_{62}FN_{10}O_{15}S$ $[M+H]+$: 1033.4095, found: 1033.4095.

Figure 3A:
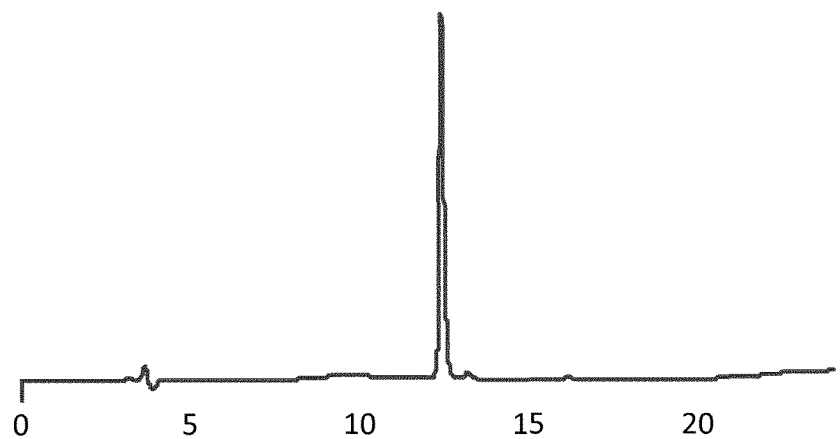
FIG. 3a is a HPLC analysis of purified peptide 14.
Figure 3B:
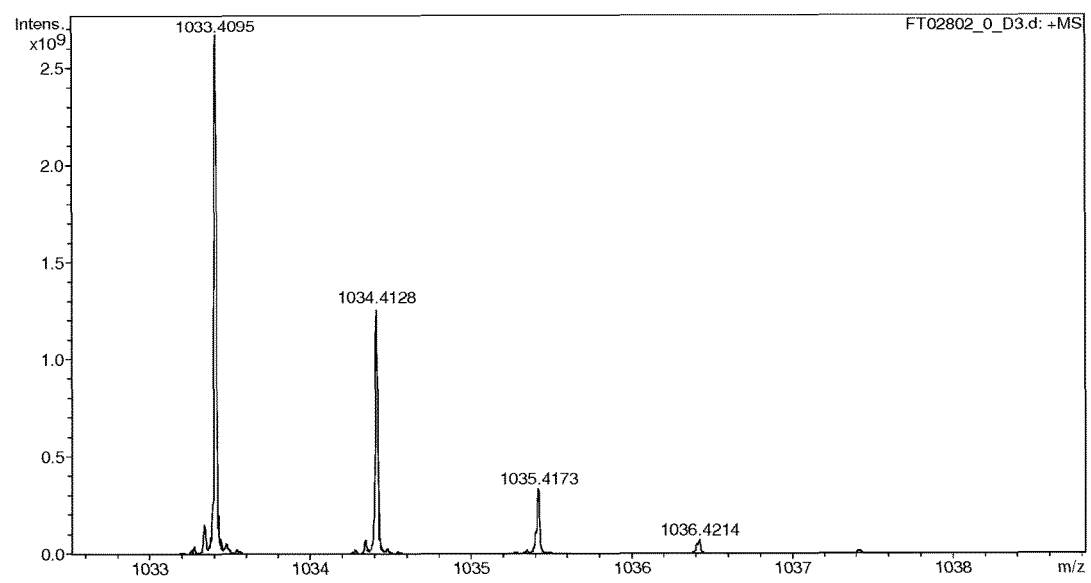
FIG. 3b is a HRMS analysis of purified peptide 14.

Analytical HPLC of purified 14: See FIG. 3a.
HRMS (MALDI) of purified 14: See FIG. 3b.

EXAMPLE 4

Ligation of Peptide Hydroxylamine 13 (SEQ ID NO 1) with Acyl Trifluoroborate 4

To peptide hydroxylamine 13 (SEQ ID NO 1; 3.9 mg, 3.8 µmol, 1.0 equiv) in a glass vial was added a 100 µM solution of acyltrifluoroborate 4 in 1:1 tBuOH/$H_2O$ with 0.1 M oxalic acid (3.8 ml, 3.8 µmol, 1.0 equiv) at room temperature. The vial was quickly shaken and the reaction was monitored by HPLC. The reaction completed within 1 h, and the mixture was directly injected to preparative HPLC using Shiseido Capcell Pak C18 column (20×250 mm) with a gradient of 20 to 70% MeCN with 0.1% TFA in 30 min. The product peak eluting at $t_R$=13.5 min was collected and lyophilized to obtain 3.1 mg of pure 14 (SEQ ID NO 2; 79% yield). Analytical HPLC and HRMS of obtained peptide were matched with those of the authentic sample.

EXAMPLE 5

Kinetic Studies with Peptide Hydroxylamine 13 (SEQ ID NO 1) and Acyl Trifluoroborate 4

All experiments were conducted in a micro vial and monitored by HPLC using 2,6-dimethylphenol as an internal standard. Peak areas in the recorded spectra were integrated and the concentration was determined from the standard curves obtained with independent experiments. (Note: No meaningful acceleration was observed in the presence of the phenol.)

(i) Pseudo-First Order Kinetics:
The following solutions were prepared in 1:1 tBuOH/$H_2O$ with 0.1 M oxalic acid: (A) 1 mM acyl trifluoroborate 4, (B) 0.2 mM peptide hydroxylamine 13 and (C) 0.5 mM 2,6-dimethylphenol. To a mixture of 200 µl solution (A), 100 µl solution (C) and 600 µl 1:1 tBuOH/$H_2O$ with 0.1 M oxalic acid in a micro vial was added 100 µl solution (B), and the vial was quickly shaken. The reaction was monitored by HPLC (50 µl injection for each run).

Logarithmic scale concentrations of 13 versus time (sec) were plotted, and the slope of their fitted curve was determined as $k_{obs}$=0.00377. From the following calculations, the second order rate constant of this reaction was determined as 19 $M^{-1}$ $s^{-1}$.

Figure 4A:
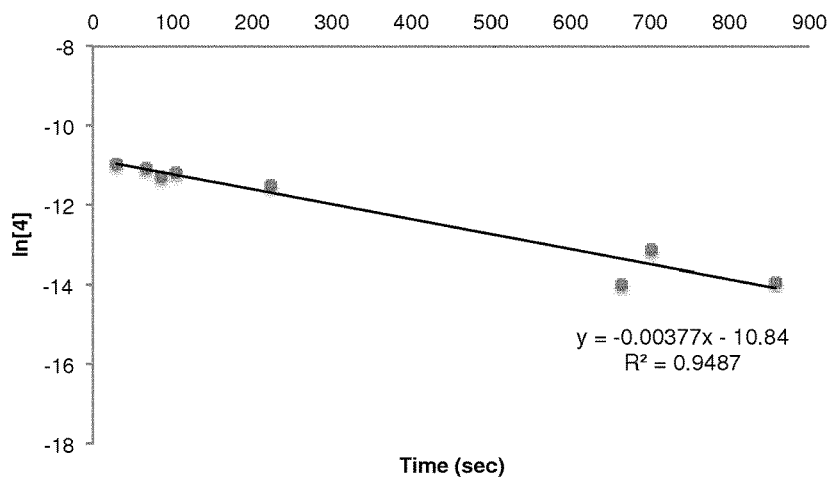
FIG. 4a is a diagram of the pseudo-first order kinetics of Example 5.

FIG. 4a: Pseudo-first order kinetics $$k_{obs}=[4]*k$$

$$k=0.00377/0.0002=18.85 \; (M^{-1}s^{-1})$$

The rate of consumption of 13 (SEQ ID NO 1) and generation of products 14 (SEQ ID NO 2) were correlated, which suggested that there is no stable intermediate involved in this ligation.

Figure 4B:
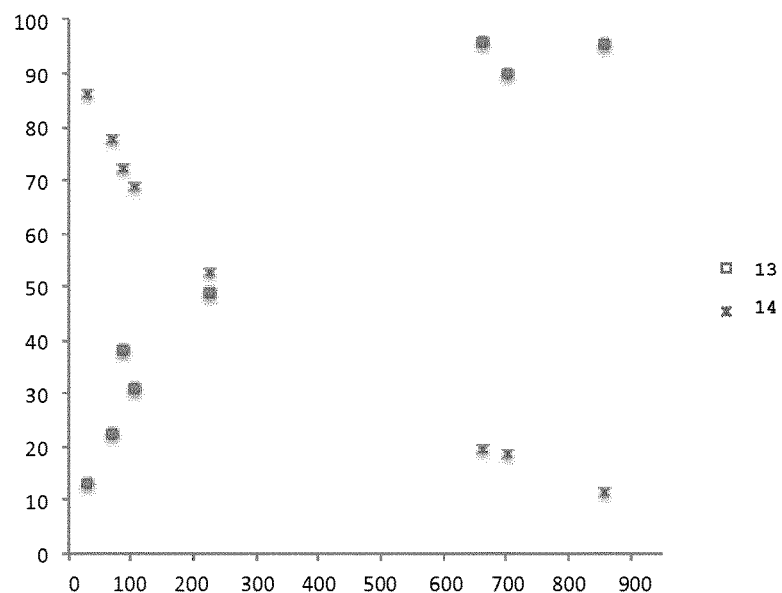
FIG. 4b is a diagram of hydroxylamine 13 and product 14 relative to the time.

FIG. 4b: Hydroxylamine 13 and product 14 vs. time (sec)

(ii) Initial Rate Kinetics:
The following solutions were prepared in 1:1 tBuOH/$H_2O$ with 0.1 M oxalic acid: (A) 0.3 mM acyl trifluoroborate 4, (B) 0.3 mM peptide hydroxylamine 13 and (C) 0.5 mM 2,6-dimethylphenol. To a mixture of 100 µl solution (A), 100 µl solution (C) and 700 µl 1:1 tBuOH/$H_2O$ with 0.1 M oxalic acid in a micro vial was added 100 µl solution (B), and the vial was quickly shaken. The reaction was monitored by HPLC (50 µl injection for each run).

The concentrations of 13 versus time (sec) were plotted, and the slope of their fitted curve was determined as 21 $M^{-1}$ $s^{-1}$.

Figure 4C:
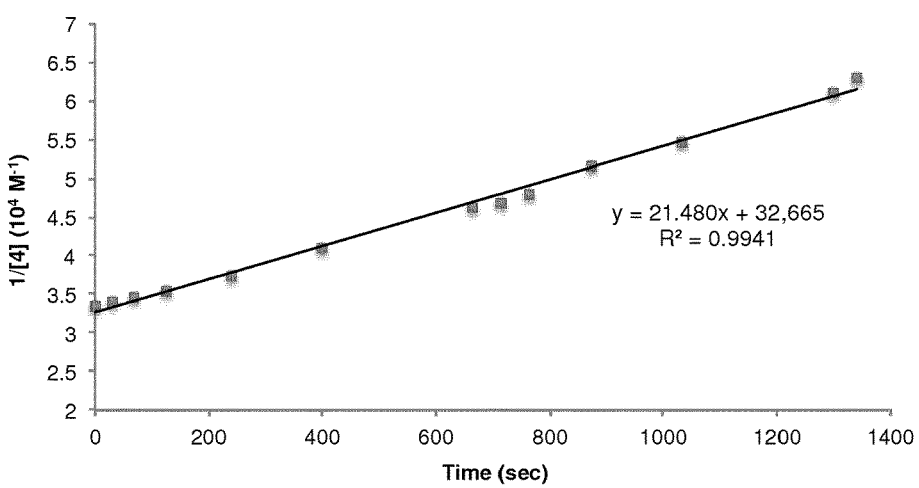
FIG. 4c is a diagram of the initial rate kinetics of Example 5.
Figure 5:
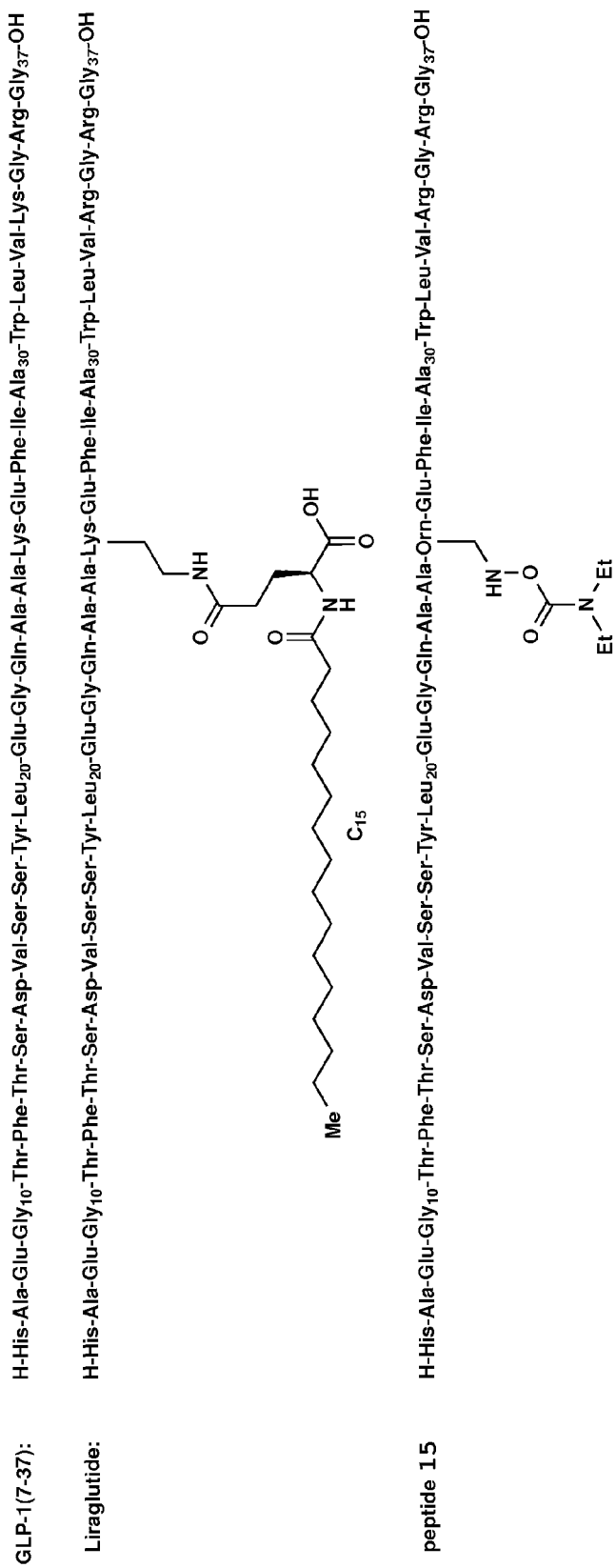
FIG. 5 is a diagram of the chemical structures of GLP-1 (7-37), Liraglutide, and peptide 15.

FIG. 4c: Initial rate kinetics
Structures of GLP-1 (7-37), Liraglutide and Peptide 15
See FIG. 5:
GLP-1 (7-37)=SEQ ID NO 3
Liraglutide=SEQ ID NO 4
Peptide 15=SEQ ID NO 5

EXAMPLE 6

Synthesis of Ornithine Hydroxylamine 19

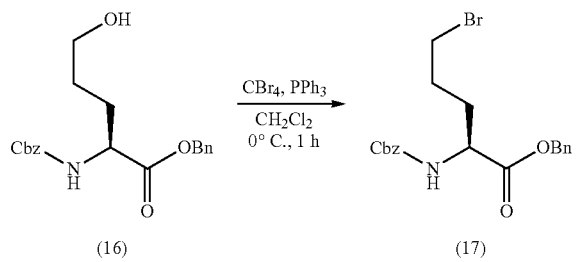

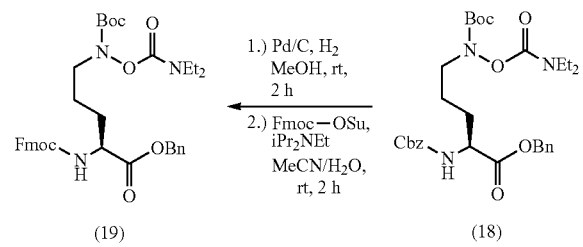

(S)-2-[N-(Benzyloxycarbonyl)amino]-5-bromopentanoic acid benzyl ester 17

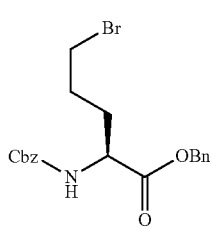

To a solution of alcohol 16 (713 mg, 1.99 mmol, 1.0 equiv) and CBr$_4$ (695 mg, 2.09 mmol, 1.05 equiv) in CH$_2$Cl$_2$ (6.6 ml) was added PPh$_3$ (576 mg, 2.19 mmol, 1.1 equiv) at 0° C., and the mixture was stirred for 1 h at the same temperature. The mixture was concentrated under reduced pressure and purified by flash column chromatography, eluting with hexane/EtGAc to give bromide 17 as a colorless oil (688 mg, 82% yield).

Colorless oil; IR (thin film) 3335, 3032, 2959, 2359, 1721, 1519, 1455, 1343, 1259, 1213, 1051 cm$^{-1}$; $^1$H NMR (400 MHz, CDCl$_3$) 7.41-7.29 (m, 10H), 5.33 (d, J=8.0 Hz, 1H), 5.21 (d, J=12.0 Hz, 1H), 5.16 (d, J=12.0 Hz, 1H), 5.11 (s, 2H), 4.50-4.40 (m, 1H), 3.44-3.30 (m, 2H), 2.09-1.75 (m, 4H); $^{13}$C NMR (100 MHz, CDCl$_3$) 172.0, 156.0, 136.2, 135.2, 128.8, 128.7, 128.7, 128.5, 128.4, 128.3, 67.5, 67.3, 53.4, 32.8, 31.5, 28.5; $\alpha_D^{27}$ (c 0.55, CHCl$_3$): −0.97; HRMS (ESI) calc'd for C$_{20}$H$_{22}$BrNO$_4$ [M+H]$^+$: 420.0805, found: 420.0803.

(S)-2-[N-(Benzyloxycarbonyl)amino]-5-[N-(tert-butoxy-carbonyl)-N-(diethylcarbamoyloxy)amino]pentanoic acid benzyl ester 18

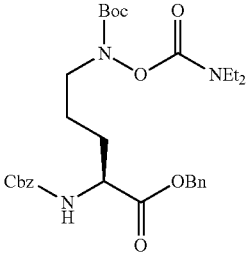

To a solution of the bromide 17 (586 mg, 1.39 mmol, 1.0 equiv) and hydroxylamine 8 (356 mg, 1.52 mmol, 1.1 equiv) in DMF (1.4 ml) was added K$_2$CO$_3$ (384 mg, 2.78 mmol, 2.0 equiv) at room temperature, and the mixture was stirred for 3 h. After the dilution with Et$_2$O, H$_2$O was added and the aqueous phase was extracted with Et$_2$G (3×). The combined organic phases were washed with brine, dried over Na$_2$SG$_4$, filtered and concentrated under reduced pressure. The crude material was purified by flash column chromatography, eluting with hexane/EtGAc to give 18 (686 mg, 86% yield).

Colorless oil; IR (thin film) 3335, 2976, 2935, 1723, 1422, 1367, 1267, 1167, 1142 cm$^{-1}$; $^1$H NMR (400 MHz, CDCl$_3$) 7.38-7.29 (m, 10H), 5.56 (d, J=7.6 Hz, 1H), 5.17 (s, 2H), 5.10 (s, 2H), 4.38 (dt, J=7.6, 12.0 Hz, 1H), 3.65 (dt, J=6.4, 7.2 Hz, 1H), 3.57 (dt, J=6.4, 7.2 Hz, 1H), 3.26 (q, J=7.2 Hz, 4H), 2.02-1.90 (m, 1H), 1.86-1.74 (m, 1H), 1.68-1.54 (m, 2H), 1.44 (s, 9H), 1.13 (brs, 6H); $^{13}$C NMR (100 MHz, CDCl$_3$) 172.3, 156.3, 155.1, 154.5, 136.5, 135.5, 128.7, 128.6, 128.6, 128.5, 128.4, 128.2, 82.0, 67.2, 67.1, 54.0, 49.7, 43.2, 41.8, 29.5, 28.3, 23.5, 14.3, 13.5; $\alpha_D^{27}$ (c 0.65, CHCl$_3$): −2.78; HRMS (ESI) calc'd for C$_{30}$H$_{41}$N$_3$O$_8$ [M+Na]$^+$: 594.2786, found: 594.2783.

(S)-5-[1-N-(tert-butoxycarbonyl)-N-(diethylcarbamoyloxy) amino]-2-[N-(9-fluorenylmethoxycarbonyl) amino]pentanoic acid 19

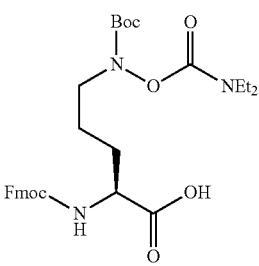

To a solution of the benzyl ester 18 (2.2 g, 3.8 mmol, 1.0 equiv) in MeOH (19 ml) was added 10% Pd/C (220 mg, 10% w/w) at room temperature, and the reaction flask was stirred for 2 h under hydrogen atmosphere. After $N_2$ was flushed into the flask, the mixture was filtered through Celite, washed with $CH_2Cl_2$ and concentrated under reduced pressure. The obtained residue was dissolved in MeCN (20 ml) and $H_2O$ (20 ml), and $iPr_2NEt$ (1.33 ml, 7.68 mmol, 2.0 equiv) and Fmoc-OSu (1.55 g, 4.60 mmol, 1.2 equiv) were added at room temperature. The mixture was stirred for 2 h. After the dilution with EtOAc, 1M aq HCl was added and the aqueous phase was extracted with EtOAc (3×). The combined organic phases were washed with brine, dried over $Na_2SO_4$, filtered and concentrated under reduced pressure. The crude material was purified by flash chromatography, eluting with hexane/EtOAc with 1% AcOH. The obtained residue was dissolved in $Et_2O$, washed with $H_2O$, dried over $Na_2SO_4$, filtered, evaporated and dried under reduced pressure to afford 19 (1.9 g, 87% yield).

Amorphous; IR (thin film) 3329, 2977, 2937, 1724, 1530, 1450, 1425, 1268, 1216, 1166 cm$^{-1}$; $^1$H NMR (400 MHz, $CD_3OD$) 7.80 (d, J=7.6 Hz, 2H), 7.69 (dd, J=7.2, 7.2 Hz, 2H), 7.40 (dd, J=7.6, 7.6 Hz, 2H), 7.31 (dd, J=7.2, 7.6 Hz, 2H), 4.39-4.32 (m, 2H), 4.27-4.15 (m, 2H), 3.64 (brs, 1H), 3.37-3.32 (m, 4H), 2.02-1.91 (m, 1H), 1.82-1.57 (m, 3H), 1.47 (s, 9H), 1.17 (brs, 6H); $^{13}$C NMR (100 MHz, $CD_3OD$) 175.6, 158.7, 156.6, 155.9, 145.2, 142.6, 128.8, 128.2, 126.3, 120.9, 83.4, 68.0, 54.9, 50.8, 48.4, 44.2, 42.9, 29.8, 28.5, 24.9, 14.5, 13.6; $\alpha_D^{27}$ (c 0.11, $CHCl_3$): +6.73; HRMS (ESI) calc'd for $C_{30}H_{39}N_3O_8$ [M+Na]$^+$: 592.2629, found: 592.2623.

EXAMPLE 7

Synthesis of Peptide 15 (SEQ ID NO 5)

Peptide 15 (SEQ ID NO 5) was synthesized on Wang-linker polystyrene resin with a loading capacity of 1.08 mmol/g. Fmoc-Gly-OH (188 mg, 0.632 mmol, 0.4 equiv to resin), HCTU (262 mg, 0.632 mmol, 0.4 equiv to resin) and NMM (139 μl, 1.26 mmol, 0.8 equiv to resin) were mixed in DMF with small amount of DMAP. The resin (1.47 g, 1.58 mmol) was treated with this solution for 36 h and the loading amount was determined as 0.36 mmol/g. The resin was treated with 20% $Ac_2O$ in DMF with small amount of DMAP for 12 h. The synthesis was performed on 0.52 mmol scale (1.46 g of resin) by automated Fmoc SPPS up to $Glu_{27}$ using the procedure described in the general methods section. At this step, 0.3 mmol of resin was separated and the Fmoc group was removed using 20% piperidine in DMF. Ornithine hydroxylamine 19 (683 mg, 1.2 mmol, 4.0 equiv to resin) was coupled to the amine using HCTU (496 mg, 1.2 mmol, 4.0 equiv to resin) and NMM (264 μl, 2.4 mmol, 8.0 equiv to resin) in DMF for 2 h. The Fmoc group was removed using 20% piperidine in DMF. Fmoc-Ala-OH.$H_2O$ (493 mg, 1.5 mmol, 5.0 equiv to resin) was coupled to the amine using HCTU (620 mg, 1.5 mmol, 5.0 equiv to resin) and NMM (330 μl, 3.0 mmol, 10 equiv to resin) in DMF for 2 h. At this step, 0.15 mmol of resin was separated and the synthesis was continued by automated Fmoc SPPS using the procedure described in the general methods section. At this step, 0.05 mmol of resin was separated and the Fmoc group was removed using 20% piperidine in DMF. The resin supported p1eptide was treated with TFA:TIPS:$H_2O$ (97:2:1) for 90 min and filtered to remove the solid support. Volatiles from the filtrate were evaporated under vacuum. The residue was triturated with MTBE and centrifuged (three cycle repeated) to obtain the crude peptide. Purification was performed by preparative HPLC using Shiseido Capcell Pak C18 column (20×250 mm) with a gradient of 20 to 90% MeCN with 0.1% TFA in 30 min. The product peak eluting at $t_R$=18.1 min was collected and lyophilized to obtain 11.2 mg of pure 15 (6.4% yield for synthesis from starting resin, cleavage and purification steps). Analytical HPLC (Shiseido C18 column with a gradient of 15 to 95% MeCN with 0.1% TFA in 20 min) and HRMS were used to confirm the purity and exact mass of the product. m/z calc'd for $C_{155}H_{235}N_{43}NaO_{49}$ [M+Na]$^+$: 3505.7111, found: 3505.7130.

Figure 6A:
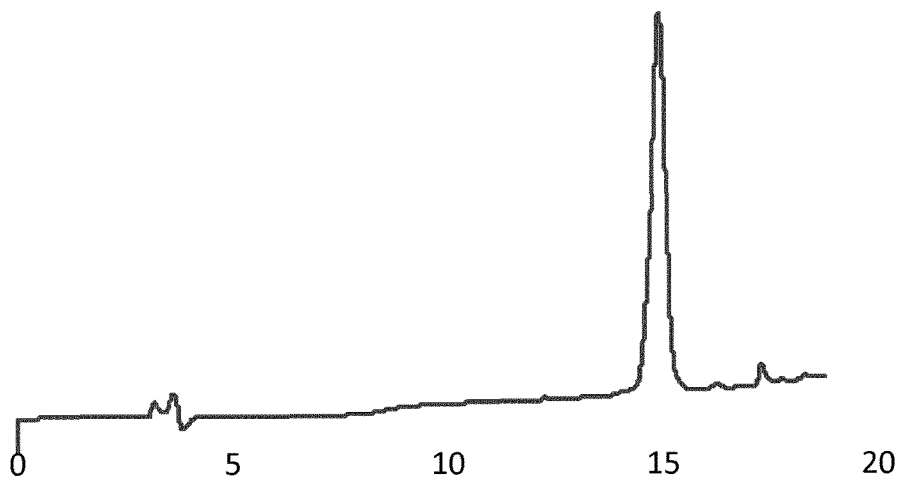
FIG. 6a is a HPLC analysis of purified peptide 15.
Figure 6B:
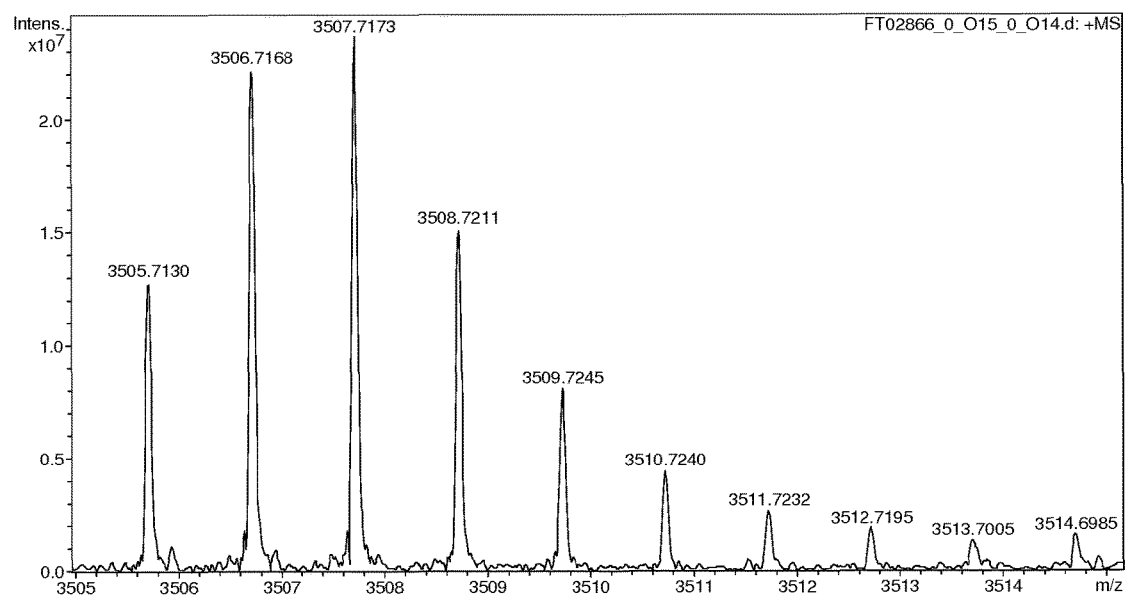
FIG. 6b is a HRMS analysis of purified peptide 15.

Analytical HPLC of purified 15: See FIG. 6a.
HRMS (MALDI) of purified 15: See FIG. 6b.

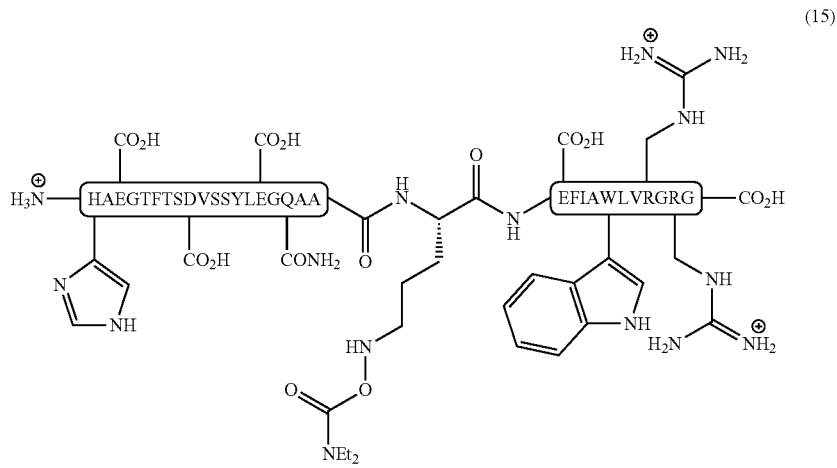

(15)

EXAMPLE 8

PEGylation of Peptide 15 (SEQ ID NO 5) with Acyl Trifluoroborates 5a and 5c to afford PEGylated Peptides 16a and 16c

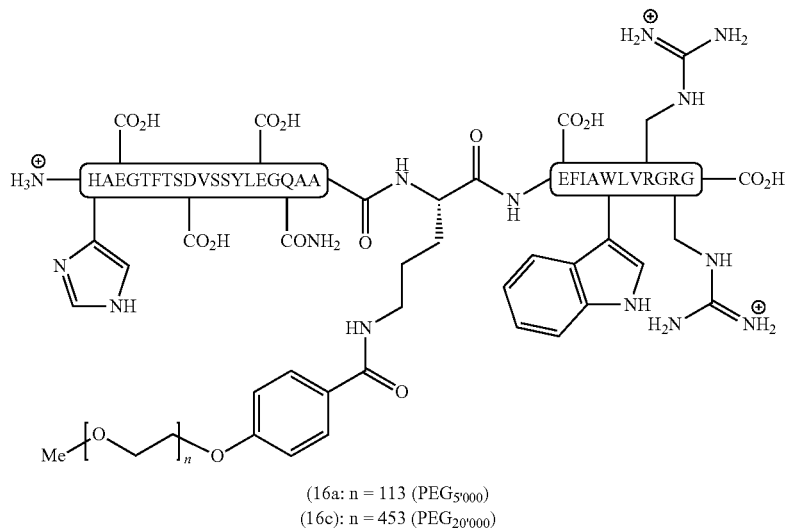

(16a: n = 113 (PEG$_{5'000}$))
(16c: n = 453 (PEG$_{20'000}$))

PEGylation of Peptide 15 (SEQ ID NO 5) with 5a:

To peptide 15 (0.48 mg, 0.14 μmol, 1.0 equiv) in an Eppendorf tube was added a solution of acyl trifluoroborate 5a in 1:1 tBuOH/H$_2$O with 0.1 M oxalic acid (1 mM, 140 μl, 0.14 μmol, 1.0 equiv). The tube was quickly shaken and left for 10 min at room temperature. Crude analytical HPLC (Shiseido C18 column with a gradient of 15 to 95% MeCN with 0.1% TFA in 20 min) showed clean conversion to 16a.

Figure 7A:
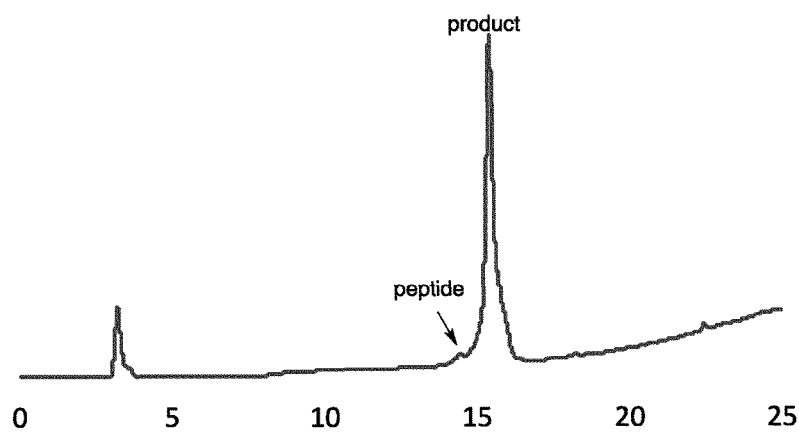
FIG. 7a is a crude HPLC analysis at 10 minutes of Example 8.
Figure 7B:
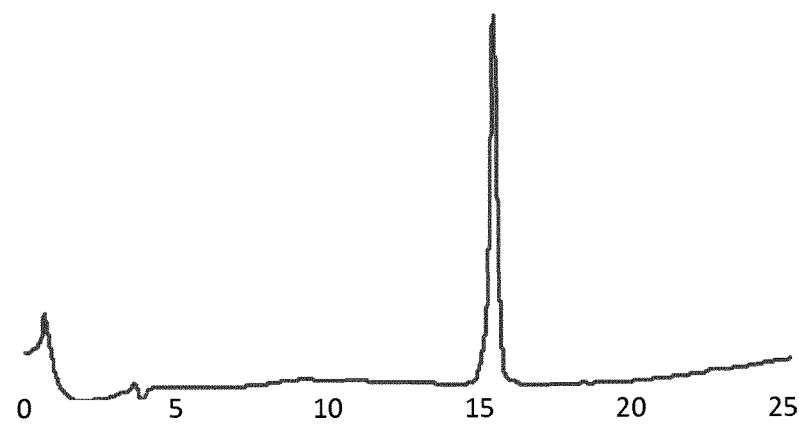
Figure 7C:
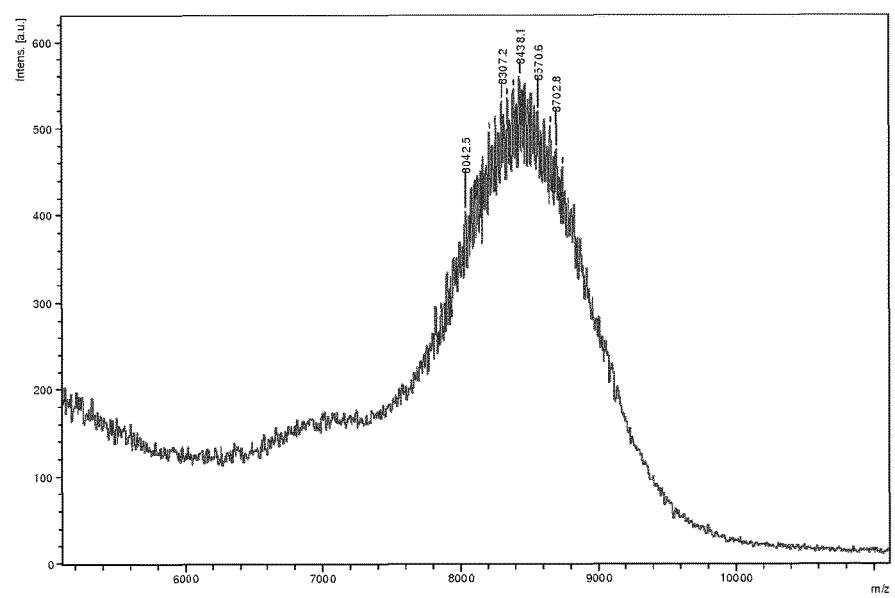

Crude HPLC trace at 10 min: See FIG. 7a.
Analytical HPLC of purified 16a: See FIG. 7b.
MALDI of purified 16a: See FIG. 7c.

PEGylation of Peptide 15 (SEQ ID NO 5) with 5c:

To peptide 15 (0.52 mg, 0.15 μmol, 1.0 equiv) in a glass vial was added a solution of acyl trifluoroborate 5c in 1:1 tBuOH/H$_2$O with 0.1 M oxalic acid (100 μM, 1.5 ml, 0.15 μmol, 1.0 equiv). The vial was quickly shaken and left for 1 hour at room temperature. Crude analytical HPLC (Phenomenex C4 column with a gradient of 15 to 95% MeCN with 0.1% TFA in 20 min) showed clean conversion to 16c.

Figure 8A:
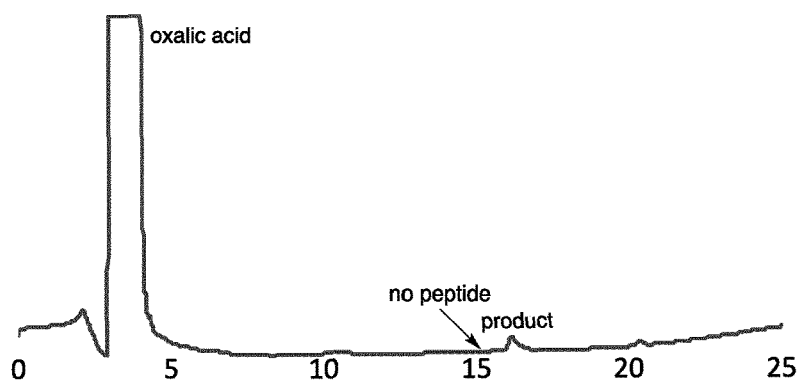
FIG. 8a is a crude HPLC analysis at 1 hour of Example 8.
Figure 8B:
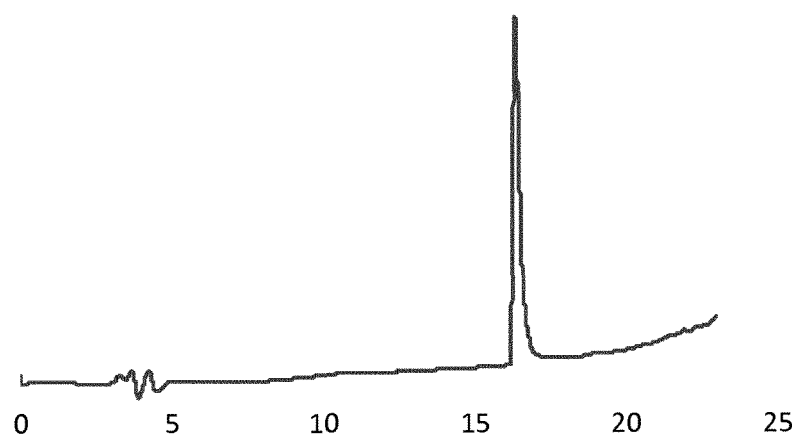
FIG. 8b is a HPLC analysis of purified PEGylated peptide 16c.
Figure 8C:
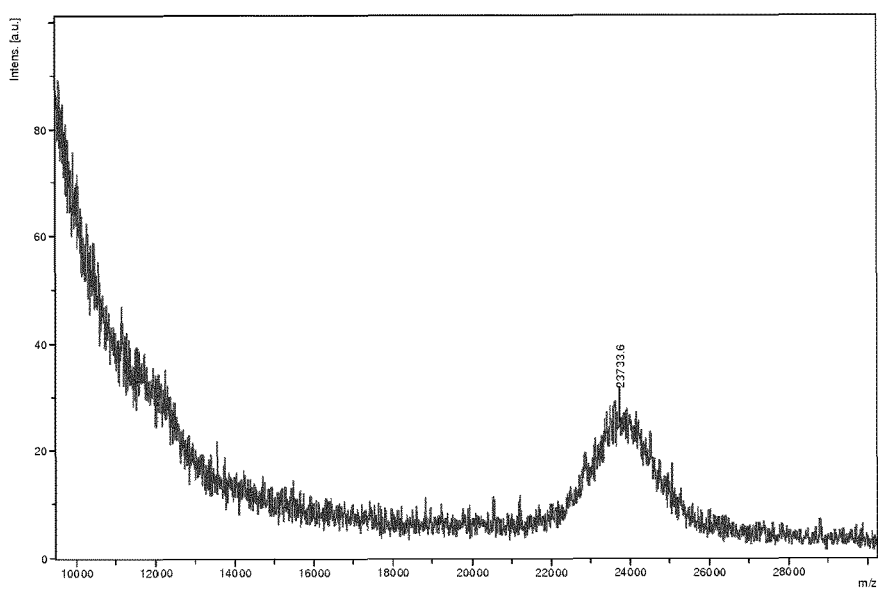
FIG. 8c is a MALDI analysis of purified PEGylated peptide 16c.

Crude HPLC trace at 1 h: See FIG. 8a.
Analytical HPLC of purified 16c: See FIG. 8b.
MALDI of purified 16c: See FIG. 8c.

EXAMPLE 9

General Procedure for the Preparation of Acyl Borates

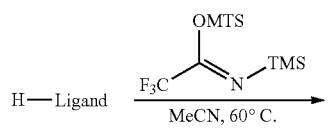

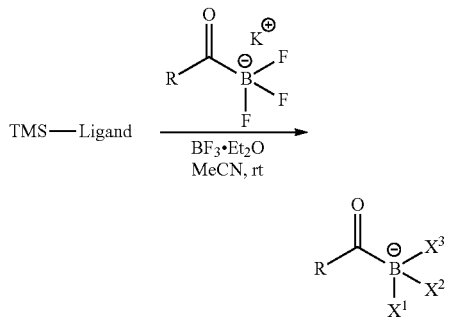

To a flame dried Schlenk flask equipped with a magnetic stirred chip was added ligand (1.0 equiv). Anhydrous MeCN (1.0 M) and N,O-bis(trimethylsilyl)trifluoroacetamide (1.2 equiv for each coordination group) were added and the mixture was stirred for 3 h at 60° C. After cooling to room temperature, all volatiles were removed carefully under vacuum and further dried for 4 h at 60° C. to give a TMS-capped ligand, which was used in next step without further purification.

To a flame dried Schlenk flask equipped with a magnetic stirred chip was added potassium acyl trifluoroborate (1.0 equiv). A solution of TMS-capped ligand (1.0 equiv) in anhydrous MeCN (0.1 M) was added. To this suspension was added BF$_3$.Et$_2$O (1.0 equiv) dropwise. The mixture became homogeneous and was stirred for 12 h at room temperature. The reaction mixture was carefully evaporated with the temperature of water bath less than 30° C. until total volume was ca. 1 ml. This solution was directly placed on silica gel column chromatography, eluting hexane/EtOAc to afford the desired acyl borate.

EXAMPLE 9a

Preparation of 4-Methylbenzoyl Borate 17

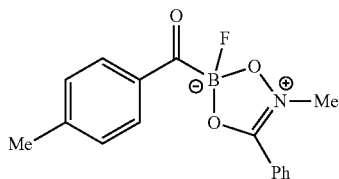

(17)

Prepared by the general procedure of Example 9 from potassium 4-methylbenzoyl trifluoroborate (230 mg, 1.0 mmol), and isolated as a white solid (37 mg, 12% yield).

$^1$H NMR (300 MHz, $d_6$-acetone) 7.97-7.89 (m, 4H), 7.81-7.75 (m, 1H), 7.72-7.64 (m, 2H), 7.31-7.27 (m, 2H), 3.91 (s, 3H), 2.38 (s, 3H); $^{19}$F NMR (282 MHz, $d_6$-acetone) −135.66; LRMS (ESI) calc'd for $C_{19}H_{16}BFNO_2$ [M+H]$^+$: 300.1, found: 300.2.

EXAMPLE 9b

Preparation of 4-Methylbenzoyl Borate 18

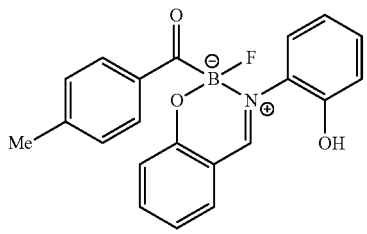

(18)

Prepared by the general procedure of Example 9 from potassium 4-methylbenzoyl trifluoroborate (230 mg, 1.0 mmol), and isolated as an orange solid (58 mg, 16% yield).

$^1$H NMR (300 MHz, CDCl$_3$) 8.40 (d, J=3.0 Hz, 1H), 8.10 (d, J=7.8 Hz, 2H), 7.59-7.54 (m, 1H), 7.30-7.22 (m, 3H), 7.19-7.13 (m, 2H), 7.09-6.89 (m, 3H), 2.39 (s, 3H); $^{19}$F NMR (282 MHz, CDCl$_3$) −147.32; HRMS (ESI) calc'd for $C_{21}H_{17}BFNNaO_3$ [M+Na]$^+$: 384.1178, found: 384.1186.

EXAMPLE 9c

Preparation of 4-Methylbenzoyl Borate 19

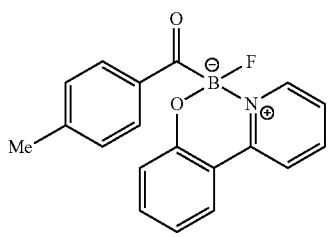

(19)

Prepared by the general procedure of Example 9 from potassium 4-methylbenzoyl trifluoroborate (230 mg, 1.0 mmol), and isolated as a pale yellow solid (120 mg, 38% yield).

IR (thin film) 3070, 2929, 2360, 1622, 1607, 1499, 1436, 1291, 1139, 1116, 1051, 761 cm$^{-1}$; $^1$H NMR (300 MHz, CD$_3$CN) 8.49 (d, J=5.7 Hz, 1H), 8.31-8.26 (m, 2H), 7.99 (d, J=8.4 Hz, 2H), 7.92 (dd, J=1.5, 8.1 Hz, 1H), 7.72-7.67 (m, 1H), 7.42-7.36 (m, 1H), 7.28 (d, J=8.4 Hz, 2H), 7.00-6.95 (m, 2H), 2.38 (s, 3H); $^{19}$F NMR (282 MHz, CD$_3$CN) −160.78; HRMS (ESI) calc'd for $C_{19}H_{15}BFNNaO_2$ [M+Na]$^+$: 342.1076, found: 342.1078.

EXAMPLE 9d

Preparation of MIDA 4-Fluorobenzoyl Borate 20

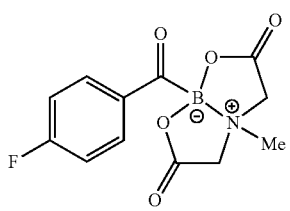

(20)

Prepared by the general procedure of Example 9 from potassium 4-fluorobenzoyl trifluoroborate (230 mg, 1.0 mmol), and isolated as a white solid (181 mg, 65% yield).

IR (thin film) 3004, 1802, 1745, 1625, 1600, 1582, 1498, 1473, 1450, 1333, 1241, 1192, 1150, 1104, 1029, 991 cm$^{-1}$; NMR (300 MHz, CD$_3$CN) 8.17-8.13 (m, 2H), 7.27-7.23 (m, 2H), 4.09 (d, J=16.5 Hz, 2H), 3.99 (d, J=16.5 Hz, 2H), 2.91 (s, 3H); $^{19}$F NMR (282 MHz, CD$_3$CN) −106.00; HRMS (ESI) calc'd for $C_{12}H_{12}BFNO_5$ [M+H]$^+$: 280.0793, found: 280.0792.

EXAMPLE 10

Reaction of an Acyl Borate with Small Molecule Hydroxylamine 21

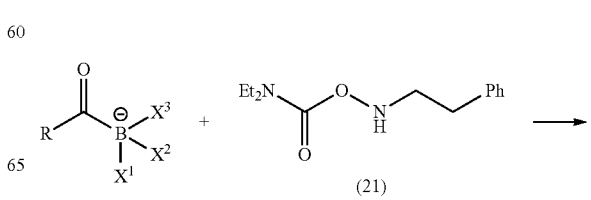

(21)

-continued

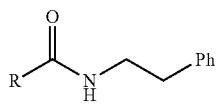

EXAMPLE 10a

Reaction of 4-Methylbenzoyl Borate 17 with Hydroxylamine 21

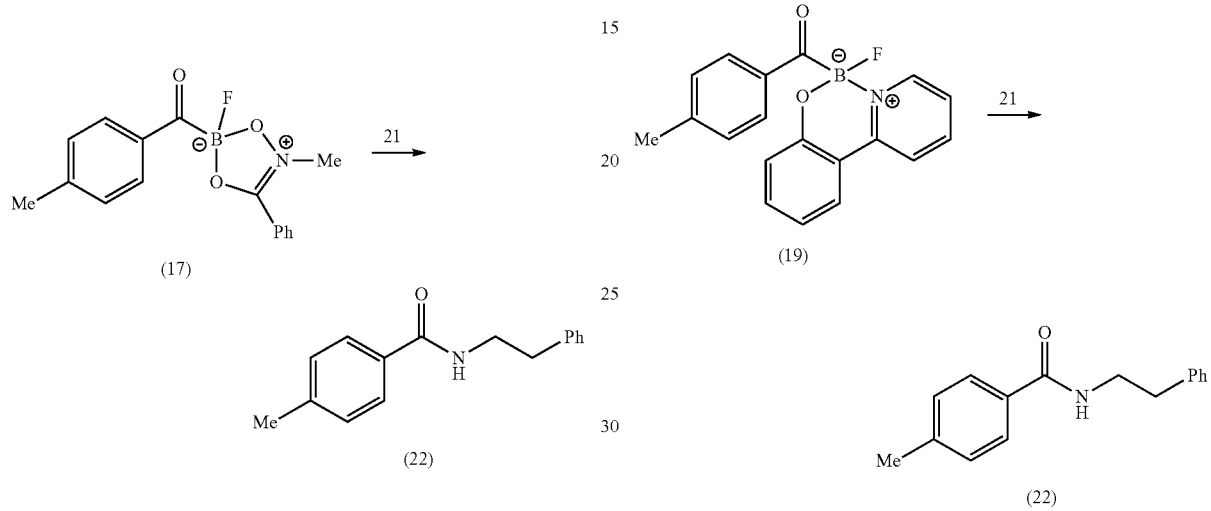

To acyl borate 17 (1.5 mg, 5.3 µmol) was added 100 mM solution of hydroxylamine 21 (53 µl, 1.0 equiv) in 1:1 MeCN/H$_2$O, and the mixture was stirred for 3 h. LC-MS analysis showed clean conversion to amide 22.

EXAMPLE 10b

Reaction of 4-Methylbenzoyl Borate 18 with Hydroxylamine 21

To acyl borate 18 (3.1 mg, 8.6 µmol) was added 100 mM solution of hydroxylamine 21 (86 µl, 1.0 equiv) in 1:1 MeCN/H$_2$O, and the mixture was stirred for 1 h. LC-MS analysis showed clean conversion to amide 22.

EXAMPLE 10c

Reaction of 4-Methylbenzoyl Borate 19 with Hydroxylamine 21

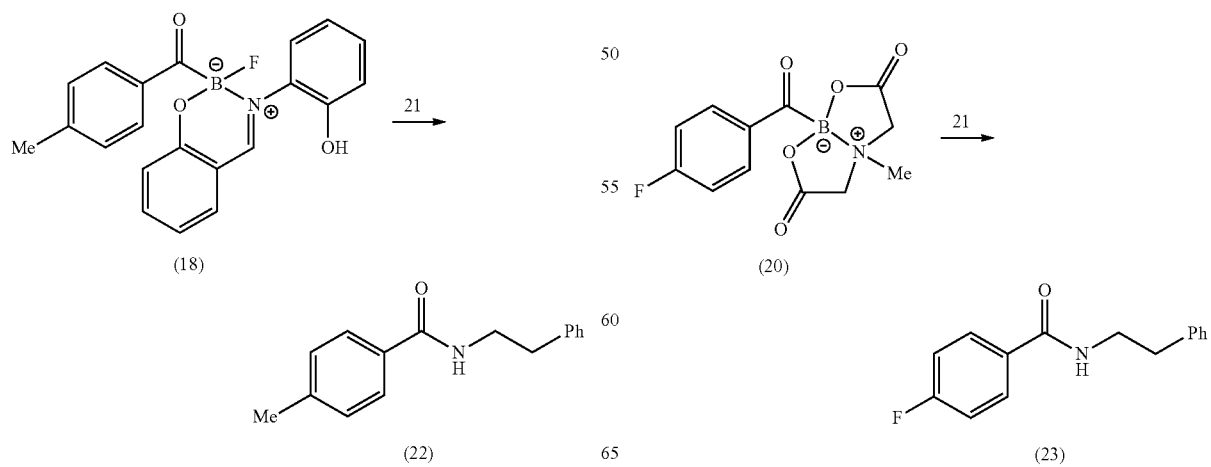

To acyl borate 19 (4.2 mg, 13.1 µmol) was added 100 mM solution of hydroxylamine 21 (131 µl, 1.0 equiv) in 1:1 MeCN/H$_2$O, and the mixture was stirred for 20 min. LC-MS analysis showed clean conversion to amide 22.

EXAMPLE 10d

Reaction of MIDA 4-Fluorobenzoyl Borate 20 with Hydroxylamine 21

To acyl borate 20 (3.8 mg, 13.6 μmol) in DMSO (50 μL) was added 136 μL of 100 mM solution of hydroxylamine 21 (1.0 equiv) in 1:1 tBuOH/H₂O, and the mixture was stirred for 10 min. LC-MS analysis showed clean conversion to amide 23.

EXAMPLE 11

Reaction of MIDA 4-Fluorobenzoyl Borate 20 with Peptide Hydroxylamine 13 (SEQ ID NO 1)

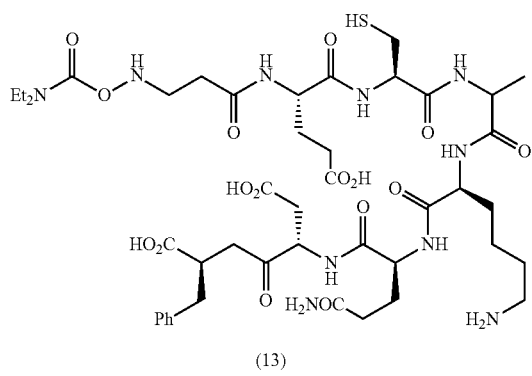

(13)

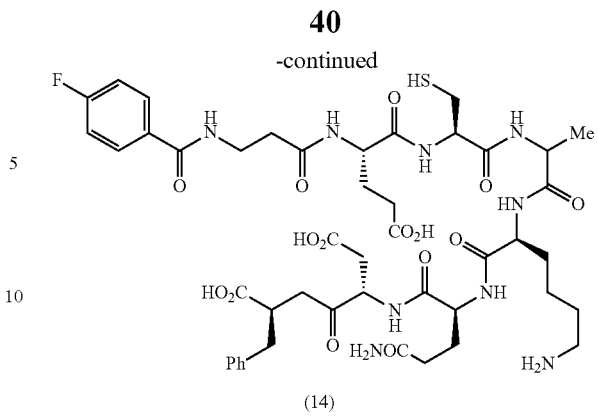

(14)

To a solution of peptide hydroxylamine 13 (SEQ ID NO 1; 3.4 mg, 3.3 μmol) in 331 μl of 1:1 tBuOH/aqueous buffer (pH 3.6, 0.1M sodium acetate/acetic acid) was added acyl borate (1.8 mg, 6.6 μmol, 2.0 equiv) in DMSO (331 μl), and the mixture was stirred for 10 min at room temperature. LC-MS analysis showed clean conversion to the amide 14 (SEQ ID NO 2).

EXAMPLE 12

Preparation of PEG-Diborate 25

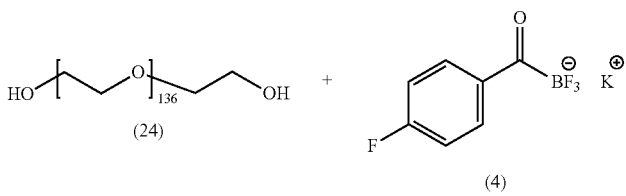

|NaH
DMSO, 80° C.

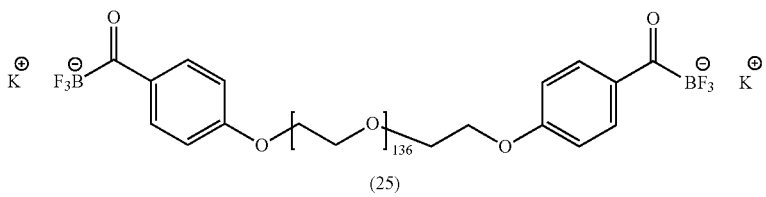

(25)

-continued

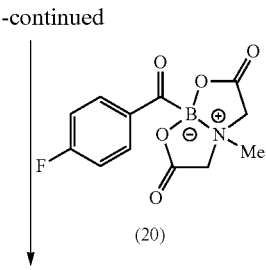

(20)

NaH (60 wt % in mineral oil, 16 mg, 0.675 mmol, 4 eq.) was added to the solution of PEG 6 kDa (24, 1 g, 0.166 mmol, 1 eq.) in dry DMSO (4 ml). The suspension was stirred for 2 h at room temperature before p-fluorophenyl acyltrifluoroborate (4, 384 mg, 1.66 mmol, 10 eq.) was added. The reaction mixture was heated to 80° C. and stirred for 25 h. The reaction mixture was cooled to room temperature and the functionalized PEG was purified by dialysis (MWCO 3500) against potassium phosphate buffer (1 l, 0.1 M, pH 7) 2×10 hours and against deionized water (1 l) 2×10 hours. The final solution was lyophilized to give PEG-diborate 25 in 87% yield (932 mg, 0.144 mmol).

$^1$H NMR: (300 MHz, CDCl$_3$): δ 8.12 (d, J=8.1 Hz, 4 H), 6.89 (d, J=8.8 Hz, 4H), 4.17 (m, 4H), 3.66-3.62 (m, ≈550 H, PEG backbone).

EXAMPLE 13

Preparation of PEG-Tetraborate 27

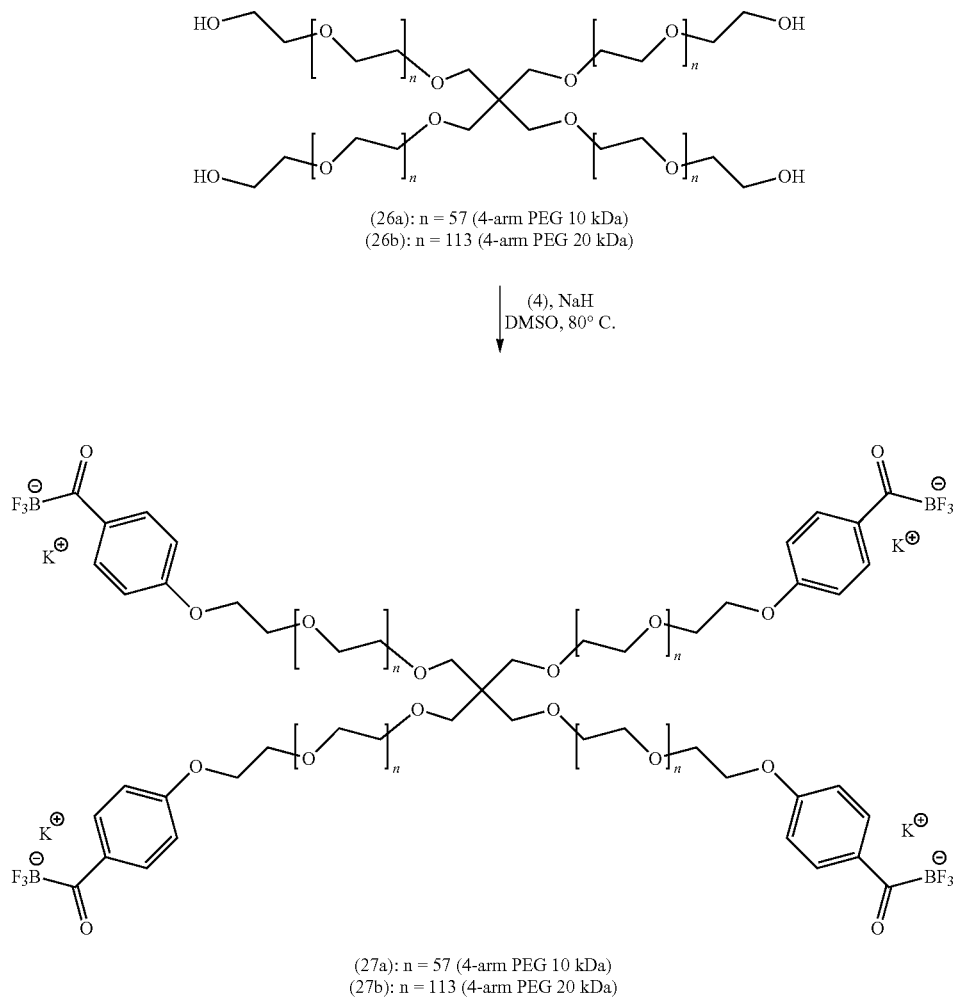

(26a): n = 57 (4-arm PEG 10 kDa)
(26b): n = 113 (4-arm PEG 20 kDa)

(4), NaH
DMSO, 80° C.

(27a): n = 57 (4-arm PEG 10 kDa)
(27b): n = 113 (4-arm PEG 20 kDa)

For 4-Arm PEG 10 kDa:

NaH (60 wt % in mineral oil, 19 mg, 0.80 mmol, 8 eq.) was added to the solution of PEG 10 kDa (26a, 1 g, 0.10 mmol, 1 eq.) in dry DMSO (5 1). The suspension was stirred for 2 h at room temperature before p-fluorophenyl acyltrifluoro-borate (4, 460 mg, 2.00 mmol, 20 eq.) was added. The reaction mixture was heated to 80° C. and stirred for 26 h. The reaction mixture was cooled to room temperature and the functionalized PEG was purified by dialysis (MWCO 3500) against potassium phosphate buffer (1 1, 0.1 M, pH 7) 2×10 hours and against deionized water (1 1) 2×10 hours. The final solution was lyophilized to give PEG-tetraborate 27a in 87% yield (870 mg, 0.087 mmol).

$^1$H NMR: (300 MHz, CDCl$_3$): δ 8.12 (d, J=8.1 Hz, 8 H), 6.89 (d, J=8.8 Hz, 8H), 4.17 (m, 8 H), 3.66-3.62 (m, ≈1000 H, PEG backbone).

For 4-arm PEG 20 kDa:

NaH (60 wt % in mineral oil, 32 mg, 0.80 mmol, 16 eq.) was added to the solution of PEG 20 kDa (26b, 1 g, 0.050 mmol, 1 eq.) in dry DMSO (5 ml). The suspension was stirred for 2 h at room temperature before p-fluorophenyl acyltrifluoro-borate (4, 460 mg, 2.00 mmol, 40 eq.) was added. The reaction mixture was heated to 80° C. and stirred for 26 h. The reaction mixture was cooled to room temperature and the functionalized PEG was purified by dialysis (MWCO 3500) against potassium phosphate buffer (1 1, 0.1 M, pH 7) 2×10 hours and against deionized water (1 1) 2×10 hours. The final solution was lyophilized to give PEG-tetraborate 27b in 83% yield (830 mg, 0.042 mmol).

$^1$H NMR: (300 MHz, CDCl$_3$): δ 8.12 (d, J=8.1 Hz, 8H), 6.89 (d, J=8.8 Hz, 8H), 4.17 (m, 8 H), 3.66-3.62 (m, ≈1800 H, PEG backbone).

The invention claimed is:

1. A polyethylene glycol substituted acyl borate of the general formula (I)

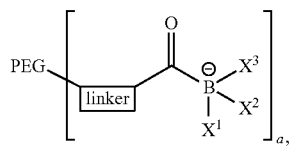
(I)

wherein

PEG denotes a polyethylene glycol-based substituent;

a is an integer from 1 to 12;

$X^1$, $X^2$, and $X^3$ are independently of one another selected from the group consisting of F, OR, $N^+R_3$, $N^+R_2OR$, $N^+R_2SR$, and $N^+R_2NR_2$, and are optionally forming a cyclic or a bicyclic structure;

R is an organic substituent or H;

the linker denotes an organic or heterorganic moiety;

the cyclic structure is a five- or six-membered heterocycle and the bicyclic structure comprises two five- or six-membered heterocycles; and the organic substituent refers to a hydrocarbon-based moiety, which is covalently attached to a remainder of a compound and which may optionally also comprise one or more heteroatoms.

2. The polyethylene glycol substituted acyl borate according to claim 1, wherein a is from 1 to 8.

3. The polyethylene glycol substituted acyl borate according to claim 1, wherein $X^1$, $X^2$, and $X^3$ are F.

4. The polyethylene glycol substituted acyl borate according to claim 1, wherein $X^1$ is F, and $X^2$ and $X^3$ are OR, and wherein $X^2$ and $X^3$ are forming a five- or six-membered heterocycle, and wherein the polyethylene glycol substituted acyl borate is selected from the group consisting of (II) to (XI)

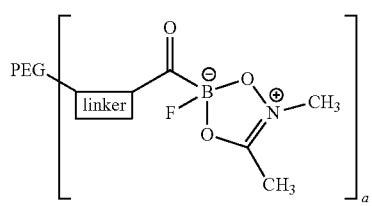
(II)

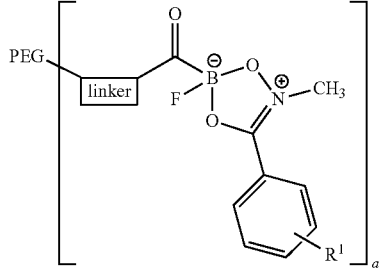
(III)

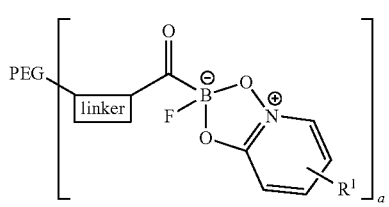
(IV)

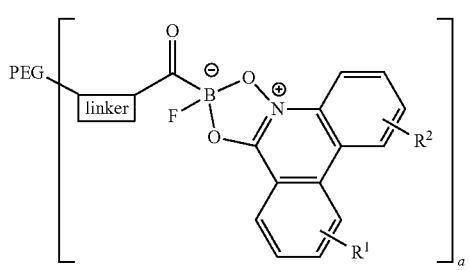
(V)

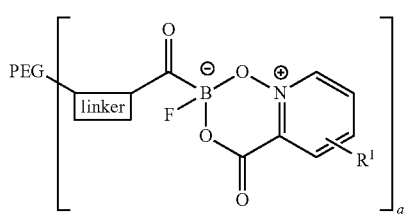
(VI)

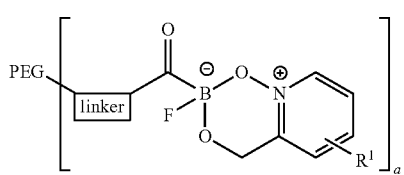
(VII)

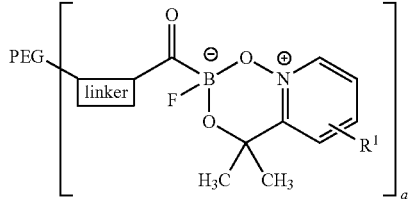
(VIII)

(IX)
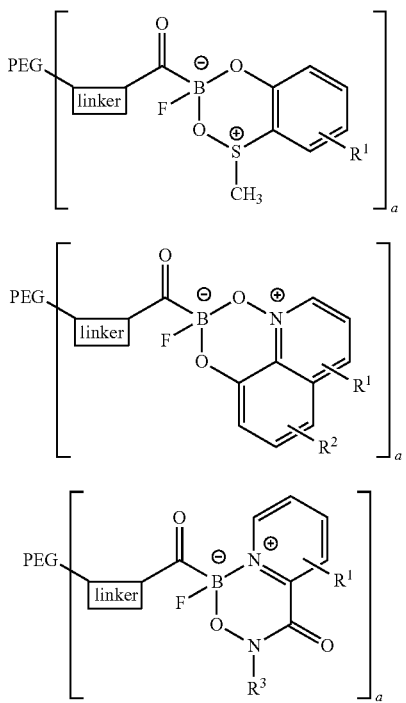

(X)

(XI)

wherein R¹ and R² are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl; and R³ is a $C_1$-$C_{16}$ alkyl.

5. The polyethylene glycol substituted acyl borate according to claim 1, wherein $X^1$ is F, $X^2$ is selected from the group consisting of $N^+R_3$, $N^+R_2OR$, $N^+R_2SR$, and $N^+R_2NR$, and $X^3$ is OR, and wherein $X^2$ and $X^3$ are forming a five- or six-membered heterocycle, and wherein the polyethylene glycol substituted acyl borate is selected from the group consisting of (XII) to (XV)

(XII)
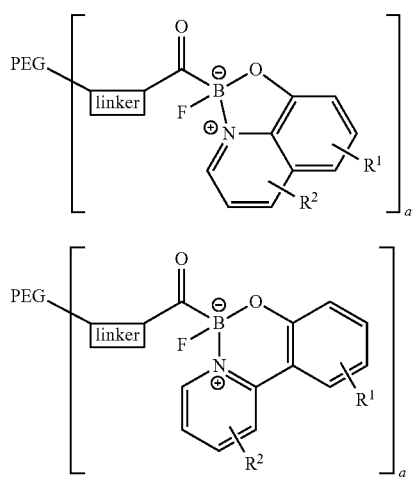

(XIII)

(XIV)
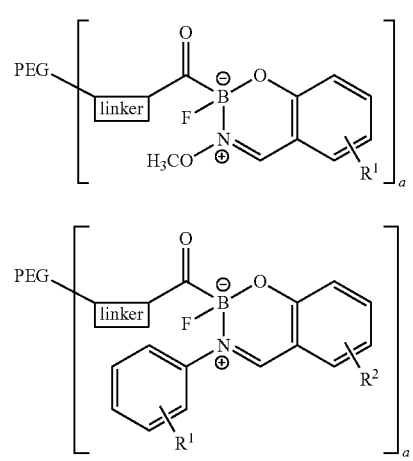

(XV)

wherein R¹ and R² are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl.

6. The polyethylene glycol substituted acyl borate according to claim 1, wherein $X^1$ and $X^3$ are OR, and $X^2$ is selected from the group consisting of $N^+R_3$, $N^+R_2OR$, $N^+R_2SR$, and $N^+R_2NR_2$, and wherein $X^1$, $X^2$ and $X^3$ are forming a bicyclic structure, and wherein the polyethylene glycol substituted acyl borate is selected from the group consisting of (XVI) to (XXXI)

(XVI)
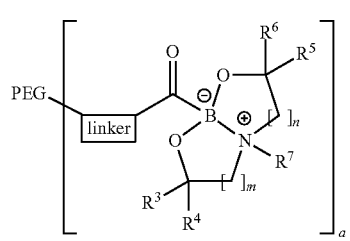

(XVII)
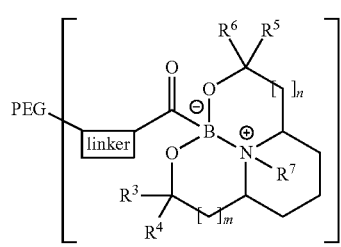

(XVIII)
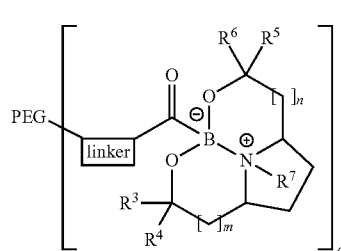

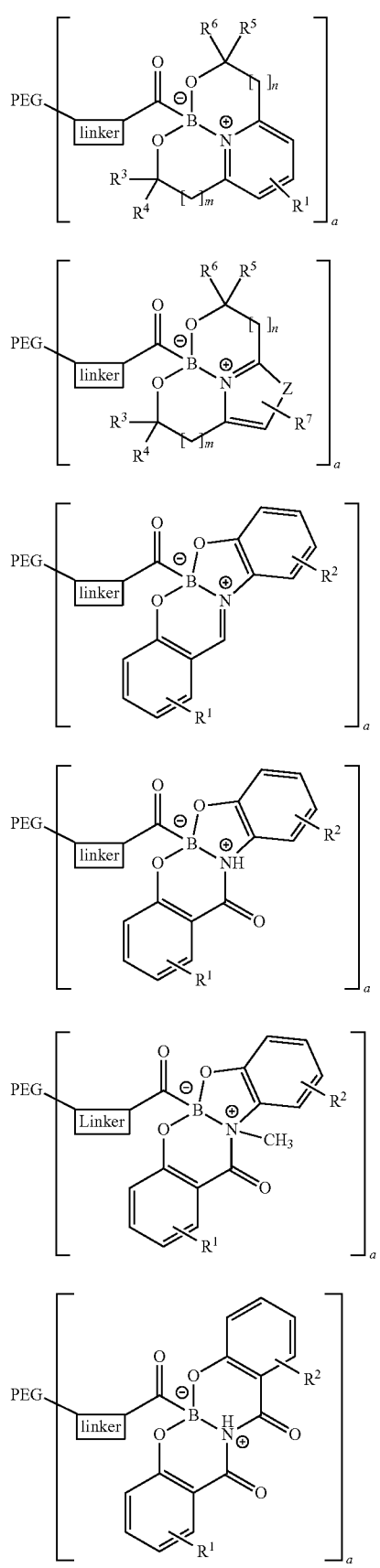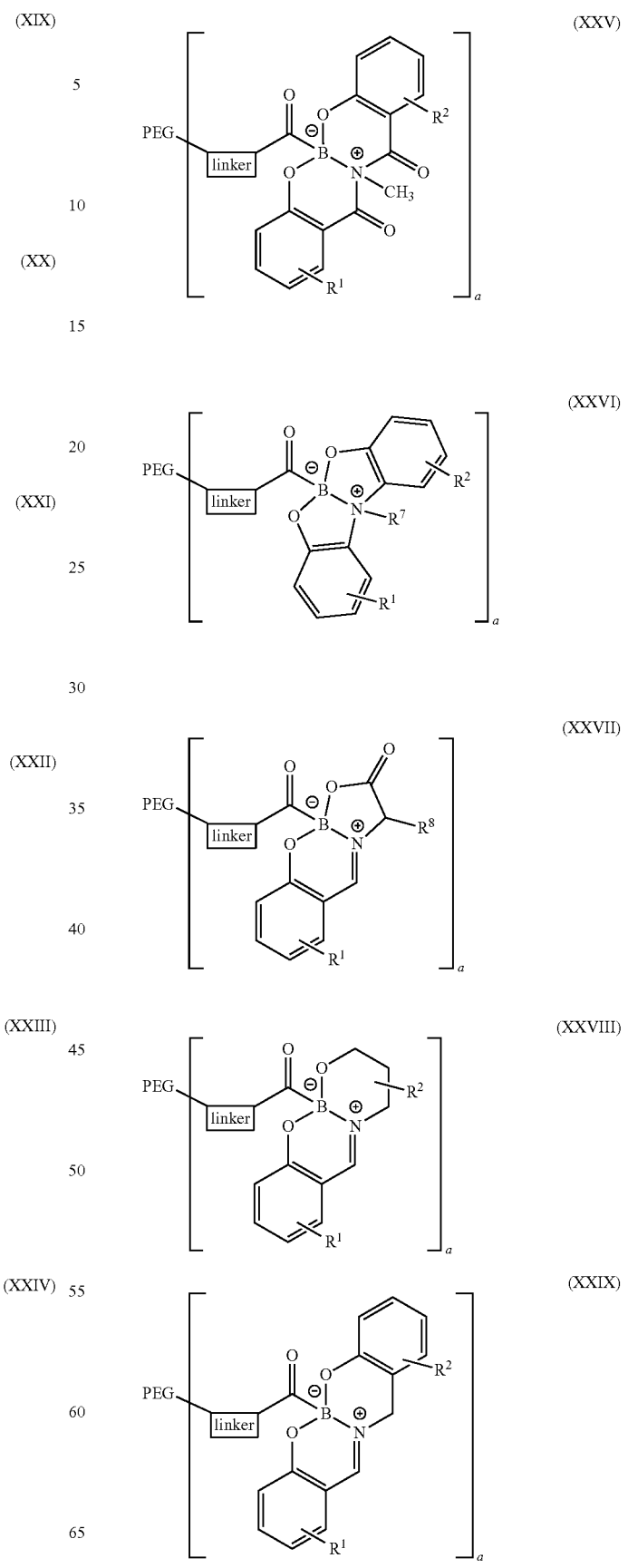

(XXX)

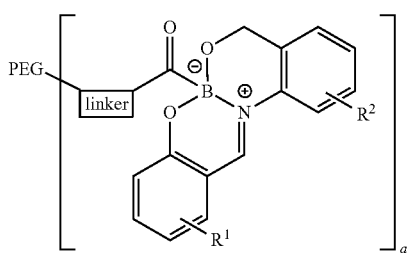

(XXXI)

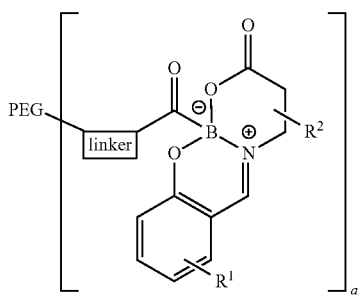

wherein
R¹ and R² are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl;
R³, R⁴, R⁵, and R⁶ are independently of one another selected from the group consisting of hydrogen, methyl, phenyl, and two geminal substituents forming a carbonyl;
R⁷ is selected from the group consisting of hydrogen, methyl, benzyl, phenyl, and substituted phenyl;
R⁸ is selected from the group consisting of hydrogen, methyl, iso-propyl, benzyl, tert-butyl, sec-butyl, iso-butyl, and substituted phenyl;
Z is selected from the group consisting of O, S, NH and $NCH_3$; and
m and n are independently of one another selected from the group consisting of 0, 1, 2, and 3.

7. The polyethylene glycol substituted acyl borate according to claim 1, wherein X¹, X² and X³ are OR, and wherein X¹, X² and X³ are forming a bicyclic structure,
and wherein the polyethylene glycol substituted acyl borate is selected from the group consisting of (XXXII) to (XXXIV)

(XXXII)

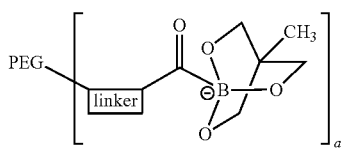

(XXXIII)

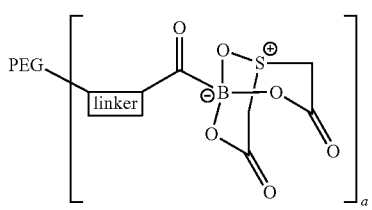

(XXXIV)

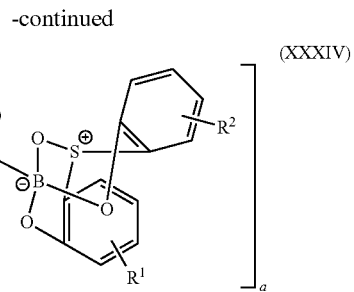

wherein
R¹ and R² are independently of one another selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl.

8. The polyethylene glycol substituted acyl borate according to claim 1, being selected from the group consisting of (XXXV) to (LV)

(XXXV)

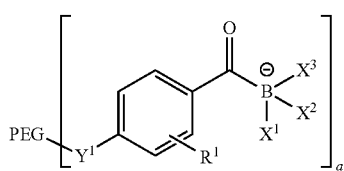

(XXXVI)

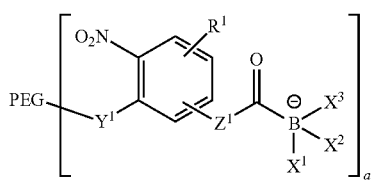

(XXXVII)

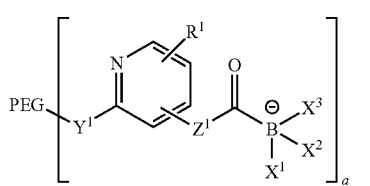

(XXXVIII)

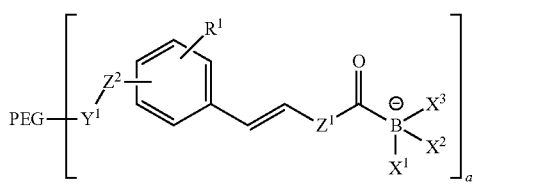

(XXXIX)

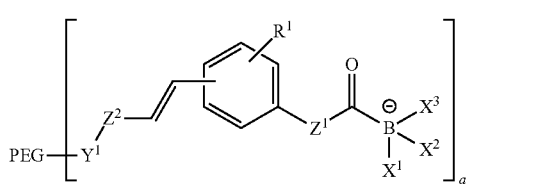

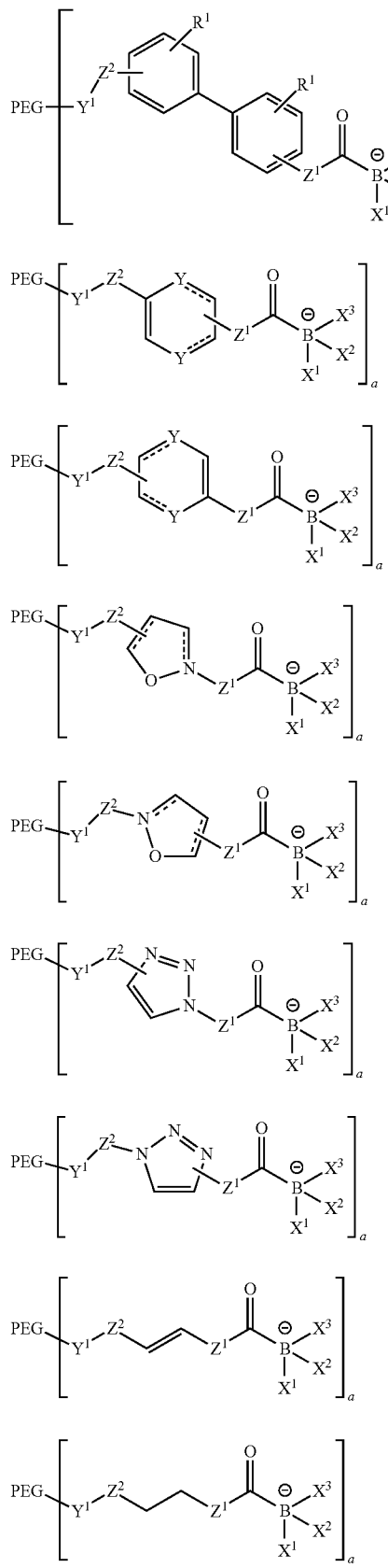
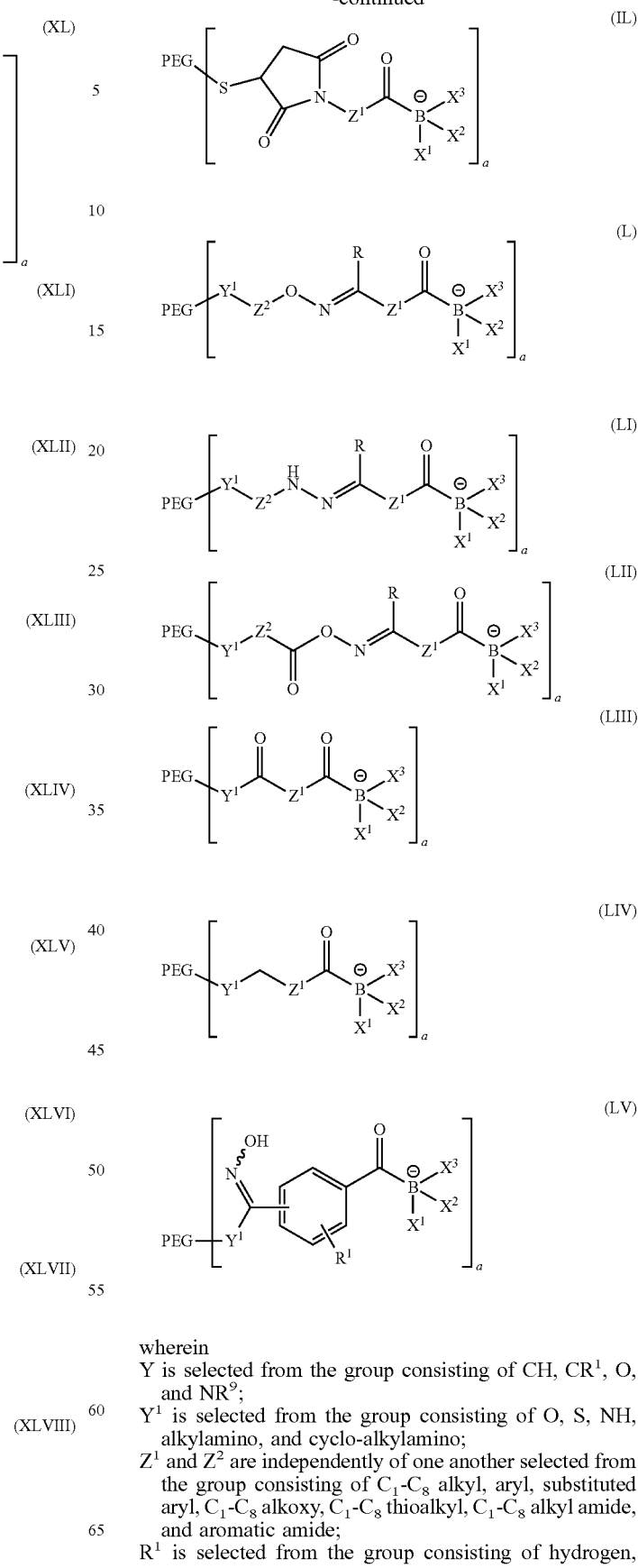

wherein
Y is selected from the group consisting of CH, $CR^1$, O, and $NR^9$;
$Y^1$ is selected from the group consisting of O, S, NH, alkylamino, and cyclo-alkylamino;
$Z^1$ and $Z^2$ are independently of one another selected from the group consisting of $C_1$-$C_8$ alkyl, aryl, substituted aryl, $C_1$-$C_8$ alkoxy, $C_1$-$C_8$ thioalkyl, $C_1$-$C_8$ alkyl amide, and aromatic amide;
$R^1$ is selected from the group consisting of hydrogen, $C_1$-$C_{16}$ alkyl, $C_1$-$C_{16}$ alkoxy, halogen, $C_1$-$C_{16}$ alkenyl, $C_1$-$C_{16}$ alkynyl, nitrile, nitro, $C_1$-$C_{16}$ aliphatic ester, amide, and $C_1$-$C_{16}$ thioalkyl; and $R^9$ is selected from the group consisting of $C_1$-$C_{16}$ alkyl, acyl, formyl, carbamoyl, aliphatic sulfonyl, and aromatic sulfonyl.

9. The polyethylene glycol substituted acyl borate according to claim 1, wherein the polyethylene glycol substituent is a linear or branched polyethylene glycol substituent of up to 200 kDa, which is optionally substituted with one or more functional groups selected from the group consisting of hydroxyl, carboxylic acid, carboxylic acid ester, amine, thiol, carbonate, carbamate, azide, alkyne, hydroxylamine, hydrazine, aldehyde, ketone, maleimide, and halogen.

10. A method for the preparation of a polyethylene glycol substituted acyl borate according to claim 1, wherein the formation of the linker involves a nucleophilic aromatic substitution reaction, a metal catalyzed cross-coupling reaction, a cycloaddition reaction, an olefin metathesis reaction, a thio-maleimide addition reaction, an oxime or hydrazine coupling reaction, or a nucleophilic addition reaction.

11. The method according to claim 10, wherein a polyethylene glycol substituted acyl borate of formula (XXXV), (XXXVI) or (XXXVII) is prepared by nucleophilic aromatic substitution; or a polyethylene glycol substituted acyl borate of formula (XXXVIII), (XXXIX) or (XL) is prepared by a metal catalyzed cross-coupling reaction; or a polyethylene glycol substituted acyl borate of one of formulas (XLI) to (XLVI) is prepared by a [4+2] or a [3+2] cycloaddition reaction; or a polyethylene glycol substituted acyl borate of formula (XLVII) or (XLVIII) is prepared by an olefin metathesis reaction; or a polyethylene glycol substituted acyl borate of formula (IL) is prepared by a thiol-maleimide addition reaction; or a polyethylene glycol substituted acyl borate of formula (L), (LI) or (LII) is prepared by an oxime or hydrazine coupling reaction; or a polyethylene glycol substituted acyl borate of formula (LIII), (LIV) or (LV) is prepared by a nucleophilic addition reaction.

12. The method for the preparation of a polyethylene glycol substituted macromolecule, the macromolecule being selected from the group consisting of synthetic, isolated, expressed or modified peptides, synthetic, isolated, expressed or modified proteins, DNA, and RNA, wherein a polyethylene glycol substituted acyl borate according to claim 1 is reacted with a hydroxylamine moiety present in the macromolecule under aqueous conditions to form an amide bond.

13. The method according to claim 12, wherein the macromolecule comprises one or more unprotected functional groups selected from the group consisting of carboxylic acid, hydroxyl, phenol, thiol, amine, ammonium, guanidine, guanidinium, imidazole, indole, and methylthio ether.

14. The method according to claim 12, wherein the hydroxylamine moiety is present at the N-terminus of the peptide or protein, at the 3'- or the 5'-end of the DNA or RNA, or on a side chain of the peptide or protein.

15. A polyethylene glycol substituted macromolecule obtainable by the method according to claim 12.

* * * * *